(12) United States Patent
Maas

(10) Patent No.: US 6,849,455 B1
(45) Date of Patent: Feb. 1, 2005

(54) ENHANCED RECOVERY OF TRANSFORMED CELLS

(75) Inventor: Renata Maas, New York, NY (US)

(73) Assignee: New York University, New York, NY (US)

( * ) Notice: Subject to any disclaimer, the term of this patent is extended or adjusted under 35 U.S.C. 154(b) by 476 days.

(21) Appl. No.: 09/888,373

(22) Filed: Jun. 26, 2001

Related U.S. Application Data

(60) Provisional application No. 60/226,673, filed on Aug. 22, 2000.

(51) Int. Cl.[7] .......................... C12N 13/00; C12N 15/74
(52) U.S. Cl. ..................... 435/471; 435/173.6; 435/461
(58) Field of Search .................................. 435/440, 471, 435/461, 252.3, 320.1, 173.6; 536/23.1

(56) References Cited

U.S. PATENT DOCUMENTS

| | | | |
|---|---|---|---|
| 5,792,633 A | * | 8/1998 | Schiestl et al. |
| 5,965,543 A | * | 10/1999 | Campisi et al. |
| 6,214,622 B1 | | 4/2001 | Treco et al. |
| 6,214,804 B1 | | 4/2001 | Felgner et al. |

OTHER PUBLICATIONS

High Efficiency Buffer Kits Feb. 2, 2001, [online], [retrieved on Dec. 13, 2002] Retrieved from EquiBio website using Internet <URL:http:/www.equibio.com/optimix.htm>.*

* cited by examiner

Primary Examiner—Remy Yucel
Assistant Examiner—Bronwen M. Loeb
(74) Attorney, Agent, or Firm—Browdy and Neimark, P.L.L.C.

(57) ABSTRACT

DNA is efficiently transformed into a host by electroporation in the presence of a methylation package, which greatly improves the efficiency of the transformation. The methylation package comprises a source of cysteine, such as cysteine, homocysteine, or glutathione, with optional iron and magnesium ions.

10 Claims, 6 Drawing Sheets

10 microns

—scL
—scH

—scL
—scH

—scL
—scH

FIG.3A
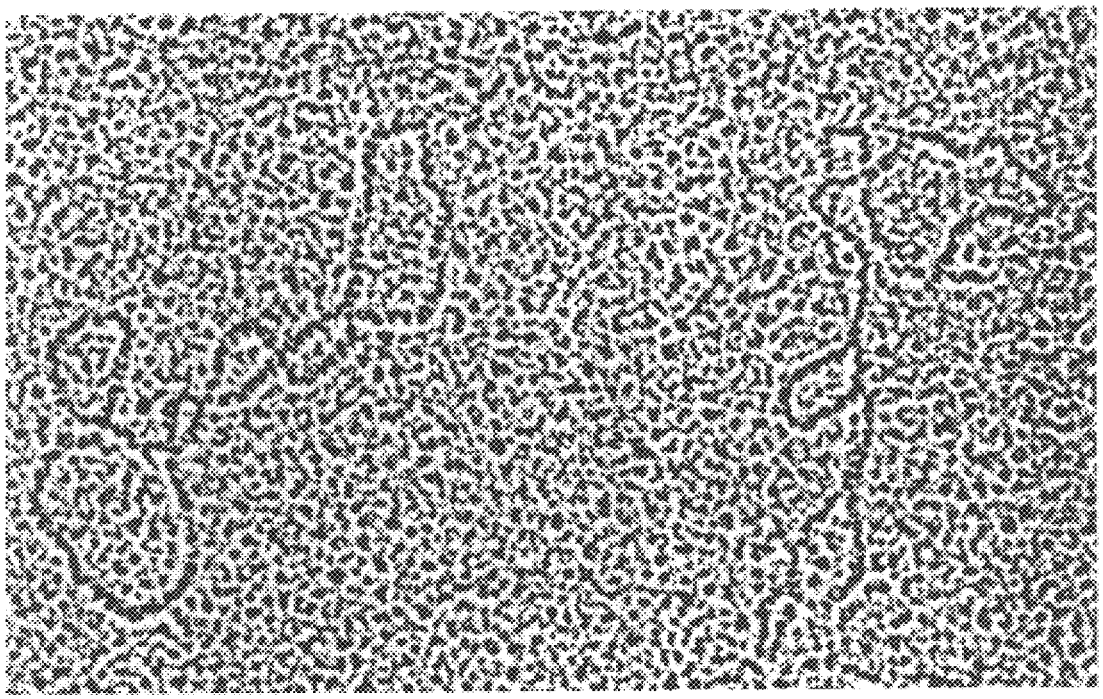
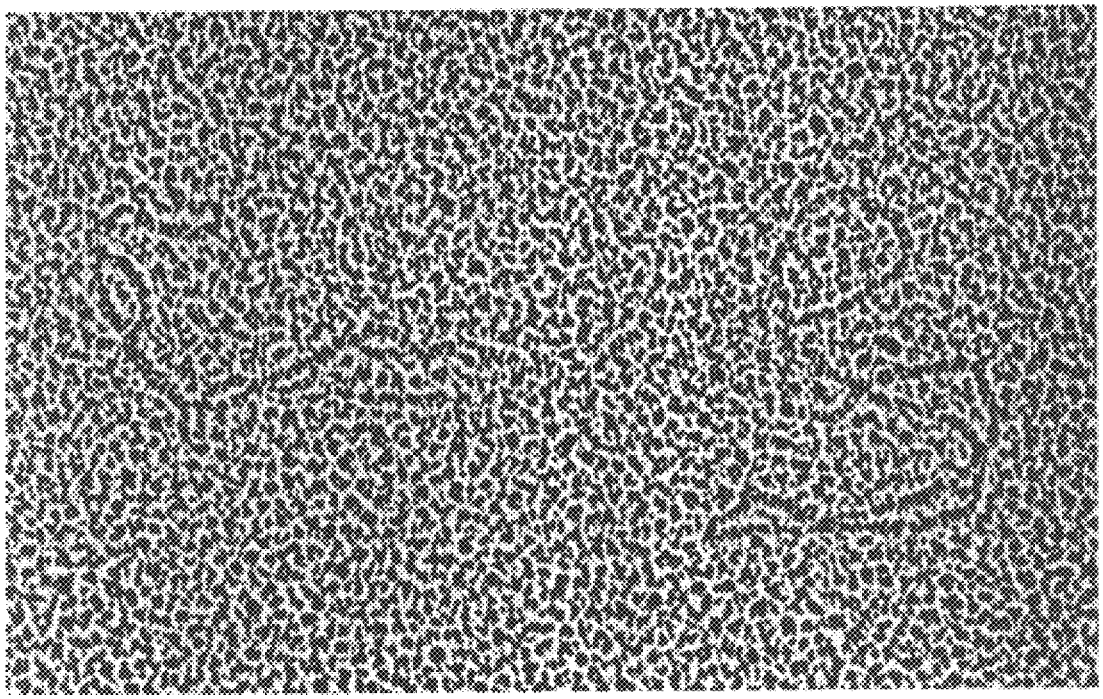
FIG.3B lon lon dam lon          dam

SEQUENCE LISTING

<160> NUMBER OF SEQ ID NOS: 4

<210> SEQ ID NO 1
<211> LENGTH: 35
<212> TYPE: DNA
<213> ORGANISM: Artificial Sequence
<220> FEATURE:
<223> OTHER INFORMATION: synthetic

<400> SEQUENCE: 1
gatccagcta tacttgtcag ggcgaattct aacta                35

```
<210> SEQ ID NO 2
<211> LENGTH: 35
<212> TYPE: DNA
<213> ORGANISM: Artificial Sequence
<220> FEATURE:
<223> OTHER INFORMATION: synthetic

<400> SEQUENCE: 2
tagccaacaa ttcagctatg cggggagtat agtta                          35

<210> SEQ ID NO 3
<211> LENGTH: 78
<212> TYPE: DNA
<213> ORGANISM: Artificial Sequence
<220> FEATURE:
<223> OTHER INFORMATION: synthetic
<221> NAME/KEY: CDS
<222> LOCATION: (1)..(72)
<223> OTHER INFORMATION:

<400> SEQUENCE: 3 atg ccc gga aaa gtt caa gac ttc ttt ctg tgc tca ctc cac ctg cgc    48
Met Pro Gly Lys Val Gln Asp Phe Phe Leu Cys Ser Leu His Leu Arg
1               5                   10                  15 att gta agt gca gga tgg tgt ggc tgaaag                             78
Ile Val Ser Ala Gly Trp Cys Gly
            20

<210> SEQ ID NO 4
<211> LENGTH: 24
<212> TYPE: PRT
<213> ORGANISM: Artificial Sequence
<220> FEATURE:
<223> OTHER INFORMATION: synthetic

<400> SEQUENCE: 4

Met Pro Gly Lys Val Gln Asp Phe Phe Leu Cys Ser Leu His Leu Arg
1               5                   10                  15

Ile Val Ser Ala Gly Trp Cys Gly
            20
```

ENHANCED RECOVERY OF TRANSFORMED CELLS

CROSS-REFERENCE TO RELATED APPLICATIONS

The present application claims priority from provisional application Serial No. 60/226,673, filed Aug. 22, 2000, the entire contents of which are hereby incorporated by reference.

This work was supported in part by NIH Grant GM06048 to Werner K. Maas. Computing resources were supported by National Science Foundation grant BIR-9318128.

FIELD OF THE INVENTION

The present invention relates to a method for increasing the number of transformed cells following electroporation.

BACKGROUND OF THE INVENTION

The ability to move DNA from one cell to another is a powerful tool in modern molecular biology and has profound practical implications for human health. Recombinant proteins produced by such manipulations are becoming widely accepted treatments for a number of human diseases and play major roles in agriculture. Though far less developed, the field of human gene therapy also has been and will continue to be influenced by improvements in technologies for manipulating DNA.

Gene therapy is a medical intervention in which a small number of the patient's cells are modified genetically to treat or cure any condition, regardless of etiology, that will be ameliorated by the long-term delivery of a therapeutic protein. Thus, almost all diseases that are currently treated by the administration of proteins, as well as several diseases for which no treatment is currently available, are candidates for treatment using gene therapy.

In somatic cell gene therapy, somatic cells (i.e., fibroblasts, hepatocytes, or endothelial cells) are removed form the patient, the cells are cultured in vitro, the gene(s) of therapeutic interest are added toe h the cells, and the genetically-engineered cells are characterized and reintroduced into the patient. The means by which these five steps are carried out are the distinguishing features of a given gene therapy system.

One example of a use of gene therapy is in treating hemophilia B, a bleeding disorder caused by a deficiency in Factor IX, a protein normally found in the blood. As a candidate for gene therapy cure, an afflicted patient would have an appropriate tissue removed (i.e., bone marrow biopsy to recover hematopoietic stem cells, phlebotomy to obtain peripheral leucocytes, a liver biopsy to obtain hepatocytes or a punch biopsy to obtain fibroblasts or keratinocytes). The patient's cells would be isolated, genetically engineered to contain an additional Factor IX gene that directs production of the missing Factor IX, and reintroduced into the patient. The patient is then capable of producing his own Factor IX and is no longer a hemophiliac.

When "cloned" libraries of genetic material are made for investigative or diagnostic purposes, total DNA is randomly digested with one or more restriction enzymes, and the DNA fragments thus made are ligated to a plasmid vector, which is capable of replicating in a host such as $E.\ coli$. The cell maintains several copies of the vector, and this makes it possible to isolate vector DNA that has the various inserted (cloned) fragments. It then becomes possible to analyze the inserted or cloned fragments for their DNA sequence and function. It is important to isolate "transformed" single colonies where each bacterium contains the same fragment and no other for the analysis, and it is also important to recover all the different fragments that have been ligated to the vector as separate colonies.

The efficient recovery of transformants under conditions where only one plasmid molecule and no other enters the transformed bacterial cell is crucial to the making of complete libraries. Plasmids known as derivatives of ColE1 are usually used as vectors, and the bacteria to be transformed are treated with an electroporator to make them permeable to entering DNA. When ColE1 derivatives and an electroporator are used, it has been found that less than 0.1% of the input DNA is recovered, making recovery very inefficient.

$E.\ coli$ plasmids of the F type were recognized as independent units of replication in the 1950s, and as [physically circular, chromosome-like elements in the 1960s. It was soon discovered that they are maintained approximately at par with the chromosome. Miniplasmids are smaller than the chromosome by a factor of $10^3$. Thus, the time that it takes to synthesize the plasmid DNA with the cellular Pol-III-dependent machine (Kornberg and Baker, 1002) is almost insignificant compared to the time it takes to synthesize the total genome of the cell.

It has been shown that when cells are synchronized for growth, all origins initiate replication synchronously (Boye and Lobner-Olesen, 1990). Replication is a complicated process that is integrated in the cell cycle. The synchronous initiation at all origins indicates that DNA synthesis starts at the same time after all cells have undergone division. This could be the result of synchronous activation of DNA synthesis at all origins, or the result of a sequestration process that prevents initiation during and after duplication of genomes (since genomes duplicate once during each cell cycle), or both. So far the only evidence that has been provided is for a sequestration mechanism (Lu et al., 1994).

Plasmids code for an origin of replication and one or more polypeptides. When a polypeptide has been shown to be absolutely required for plasmid DNA synthesis it has been considered an initiator of replication. The function performed by plasmid "initiators of replication" has thus far not been clarified. The organization of the miniplasmid RepFIC is a member of the IncFII class. Both the region labeled ori (Masai et al., 1983) and the protein RepA have been shown to be essential (Maas et al., 1991).

SUMMARY OF THE INVENTION

It is an object of the present invention to overcome the aforesaid deficiencies in the prior art.

It is another object of the present invention to make cloned libraries in the most efficient way.

It is a further object of the present invention to transfer DNA by electroporation in an efficient and replicable process.

It is another object of the present invention to provide improved recognition and selection of transformed clones following transfer of DNA by electroporation.

According to the present invention, DNA is transferred by electroporation into a host such as $E.\ coli$ in an improved percentage by (1) adding cysteine to selective plates; (2) adding homocysteine, iron and magnesium supplements immediately after electroporation and to the selective plates, or (3) adding homocysteine, iron and magnesium supplements together with glutathione, which is a source of cysteine. The state of conditions used totally depends on the conformation of the DNA that is being transferred and whether it has particular peptides associated with it.

Additionally, when RepFIC is used to transform competent hosts under conditions where the synthesis of plasmid-encoded polypeptides is expected to increase, the plasmid is maintained in an altered structural form. The altered structure can be used directly in transformations, suggesting that it is a normal precursor. Plasmid in the altered structural form is extremely sensitive to digestion by DpnI, which recognizes fully methylated DNA. Preliminary analysis suggested that the DNA was fully methylated in the origin regions at closely spaced loci. The hypermethylated and altered structure was stabilized in lon hosts. Methylation required E. coli adenine methylase (dam) in vitro. In this case, dam-methyltransferase methylates non-canonical sequences, as there are no canonical GATCs in the entire origin region. Methylation depends on the DNA conformation both in vivo and in vitro, but the conformation is independent of methylation. Thus, is appears that methylation occurs after the initiation-related conformational shift.

Conventionally, bacteria that have been transformed for a particular trait such as resistance to an antibiotic are spread onto plates containing that antibiotic. They are then "purified" and investigated further. It has been found that when $10^{10}$ molecules of DNA are injected into E. coli by electroporation, less than 0.0005% of the DNA molecules recovered as transformed bacteria.

In studying and determining the factors that were limiting the recovery of transformed bacteria, it was found that approximately 20% of the DNA used in the electroporation process could be recovered as transformations. This improvement results in the recovery of 100,000 times as many transformants as could heretofore be recovered. This level of efficiency makes any diagnostic treatment or research scheme that depends on DNA shotgun cloning, such as used in generating genomic libraries, or any specific cloning of DNA fragments, easy to perform as well as very efficient.

BRIEF DESCRIPTION OF THE DRAWINGS

FIG. 3A shows plasmid DNA from normal C600 hosts.

FIG. 3B shows plasmid DNA from C600 hosts containing imprinted scL plasmid.

In FIGS. 3A and 3B DNA was spread for electron microscopy from droplets by the cytochromec method.

FIG. 4A, lanes 1, 2, and 3, scH DNA treated respectively as follows: untreated, MboI and DpnI. Lanes 4, 5, and 6, scL DNA treated respectively as follows: unbtreated, MboI and DpnI.

FIG. 4B, lanes 1, 2, and 3, scH DNA treated respectively as follows: untreated, DpnI, and DpnII. Lanes 4, 5, and 6, scL DNA treated as follows: untreated, DpnI, and DpnII. Lane 7, molecular weight markers.

FIG. 4C, restriction of scL DNA isolated from a lon strain, a dcm strain (marker); lane 2, scL DNA from a lon host; lane 3, lane 2 DNA restricted with DpnI; lane 4, mostly scL DNA from a dam host; lane 7, lane 6 DNA treated with DpnI.

FIG. 4D shows scH and scL DNAs from a dam host were methylated with dam-methyltransferase in vitro. Lanes 1 and 4, undigested; lanes 2 and 5, restricted with DpnI. Lane 3, restricted with MboI.

FIG. 4E, the susceptibility to degradation by piperidine of scL DNA isolated from a lon host (lane 1) and a mixtures of scL and scH DNA isolated from a dcm host (lane 5). Piperidine treatment was as follows: lanes 1 and 5, none; lanes 2 an 6, 7 minutes; lanes 3 and 7, 15 minutes; lanes 4 and 8, 30 minutes, with all piperidine treatments conducted at 86° C.

FIG. 5A shows DNA as isolated from a lon host grown to stationary phase with homocysteine in lane 1, homocysteine and ferrous sulfate in lane 2, homocysteine and magnesium sulfate in lane 3, and no supplements in lane 4. Glycerol was used as a carbon source in all cases. In lanes 5, 6 and 7, the DNAs shown in lanes 1, 2, and 3 were restricted with DpnI for 30 minutes.

In FIG. 5B, samples shown in FIG. 5A lanes 1, 2, and 3 were treated for 30 minutes with ExoIII, ibn that order. Odd number lanes were incubated with ExoIII buffer as supplied. The even number lanes were incubated with ExoIII and buffer.

FIG. 5C illustrates DNA isolated from a dam host grown with the same media and supplements as the lon host in FIG. 5A, lanes 1, 2, and 3, in the same order. Odd number lanes were incubated with ExoIII buffer as supplied. The even number lanes were incubated with ExoIII and buffer.

FIG. 5D illustrates DNAs isolated from a lon host (lanes 1, 2, 3 and 4) and from a dam host (lanes 5, 6, 7 and 8). Lanes 1 and 5 were incubated with ExoIII buffer as supplied. Lanes 2 and 6 were incubated with ExoIII buffer as supplied and ExoIII for 30 minutes at 37° C. All other lanes: treated as lanes 2 and 6, then partially inactivated at 65° C. for 10 minutes. This was followed by treatment with 12 mM $Mg^{++}$ at 37° C. for 45 minutes (lanes 3 and 7) or 12 mM $Mg^{++}$ at 37° C. for 45 minutes.

DETAILED DESCRIPTION OF THE INVENTION

Figure 1:
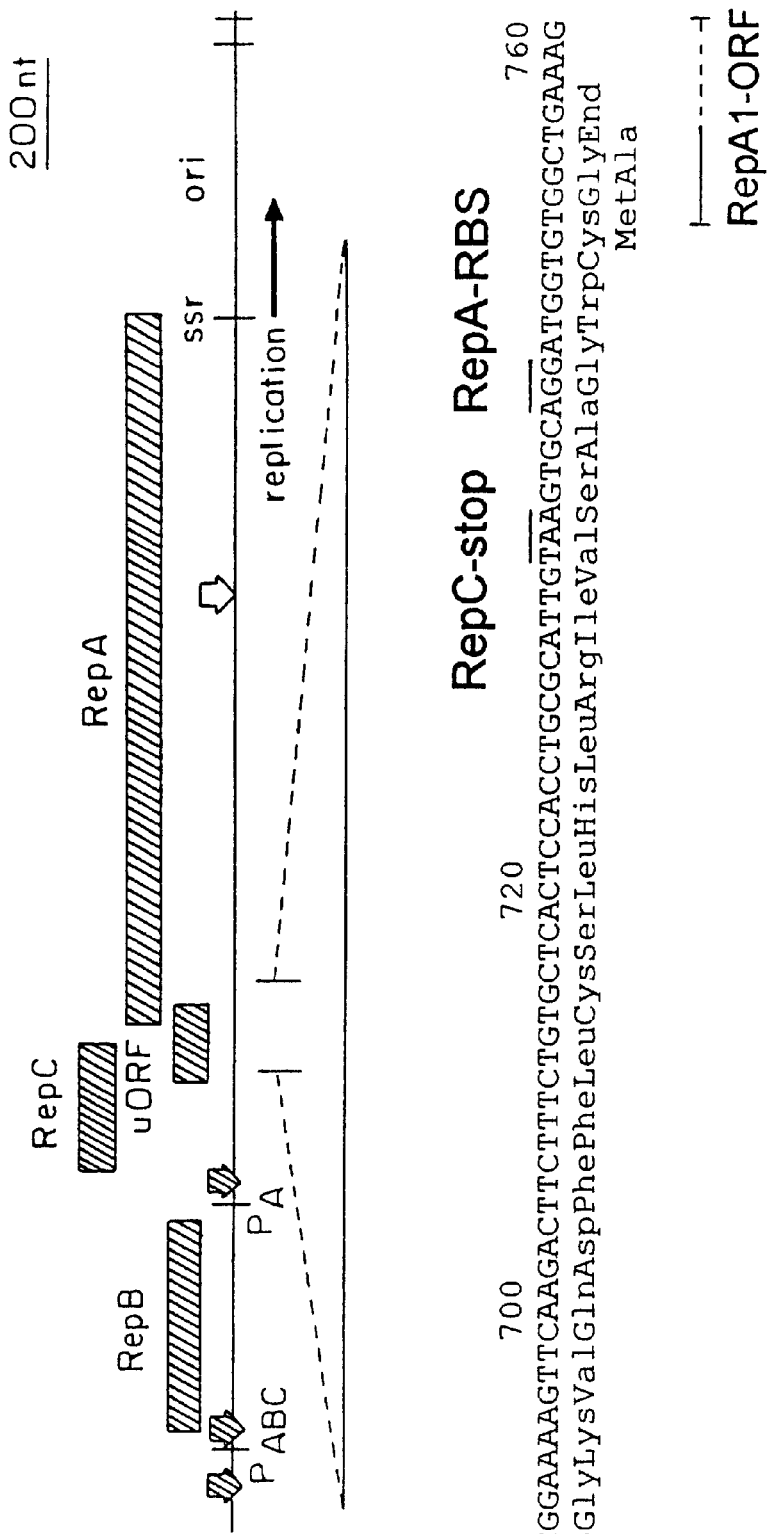
FIG. 1 is a map of the replicon RepFIC region (SEQ ID NO: 3) drawn to scale. The horizontal arrow indicates the direction of replication and of transcription-translation. The grey rectangles represent all expressed polypeptides. Coupled translation via a cysteine-methionine frameshift is enlarged for detail and shown below the map. The short vertical arrows indicated unique replicon GATC (dam) sites. The left-most site is located ten nucleoside upstream of the $-35$ $P_{ABC}$ promoter sequence. The right-most dam site is located two nucleoside downstream of the $-10$ $P_A$ promoter sequence.

When RepFIC is used to transform competent hosts under conditions where the synthesis of plasmid-encoded polypeptides is expected to increase, the plasmid is maintained in an altered structural form. The altered structure can be used directly in transformations, suggesting that it is a normal precursor for replication. Plasmid in the altered structural form was further analyzed and proven to be extremely sensitive to digestion by DnpI, which recognizes fully methylated DNA. Preliminary analysis suggested that the DNA was fully methylated in the origin region at closely spaced loci. The hypermethylated and altered structure was stabilized in lon hosts. Methylation required $E.$ $coli$ adenine methylase (dam) in vivo, and could be reconstituted by dam-methyltransferase in vitro. In this case, dam-methyltransferase methylates non-canonical sequences, as there are no canonical GATCs in the entire origin region. Methylation was dependent on the DNA conformation both in vitro and in vivo, but the conformation was independent of methylation. Thus, methylation appears to occur after the initiation-related conformational shift.

The significantly large improvement in recovery of transformed cells obtained in the present invention involves the transfer of DNA by electorporation into $E.$ $coli$ and the subsequent recognition and selection of transformed clones of the organism. Usually bacteria that have been transformed for a particular trait, such as resistance to an antibiotic, are spread on plates containing that antibiotic, and then they are purified and investigated further. A simple calculation disclosed that when $10^{10}$ molecules of DNA are injected into $E.$ $Coli$ by electroporation, less than 0.0005% of the DNA molecules are recovered as transformed bacteria. The present inventors studied and determined the factors that were limiting the recovery of transformed bacteria, and learned that approximately 20% of the DNA used in the electroporation process could, in fact, be recovered as transformants. This improvement, which results in the recovery of 100,0000 times as many transformants as before, can be attained by:

1. Adding cysteine to the selective plates;
2. Adding homocysteine, iron and magnesium supplements immediately after electroporation and to the selective plates; or
3. Adding iron and magnesium supplements together with glutathione, which is a source of cysteine.

The conditions for optimum efficiency depend totally on the conformation of the DNA that is being transferred, and whether it has particular peptides associated with it.

The method of the present invention makes any diagnostic or research scheme dependent on DNA shotgun cloning, such as used in generating genomic libraries, or any specific cloning of DNA fragments, easy to perform and efficient.

When a plasmid has been transferred into cells by electroporation, replication of the plasmid and subsequent cell division take place under stress. This is demonstrated by the low recovery of transformants, despite the fact that electroporation is an extremely efficient process.

The experiments described below were carried out to demonstrate the efficacy of cysteine in relieving this stress. Table 1 illustrates that adding cysteine is important when a vector is used and that is depends on the synthesis of initiator proteins for getting started or established.

TABLE 1

Transformation by electroporation of C600
(*$3 \times 10^9$ cells per transformation) with various replicons

| Plasmid replicon | Input (f-moles) | Input (molecules) | Cysteine in selective medium | Number of transformants | % recovery |
|---|---|---|---|---|---|
| RepFIC | **17 | $10^{10}$ | yes | $1.9 \times 10^9$ | 20 |
|  |  |  | no | $5.0 \times 10^3$ | — |
| RepFIB | 25 | $1.5\ 10^{10}$ | yes | $1.0 \times 10^8$ | 0.7 |
|  |  |  | no | $1.9 \times 10^5$ | — |
| pUC- | 25 | $1.5\ 10^{10}$ | yes | $5.0 \times 10^5$ | 0.003 |
|  |  |  | no | $5.0 \times 10^5$ | 0.003 |

*Calculated from total number of colony forming units after electroporation.
**Lower DNA inputs were less efficient. Higher inputs (within the same order of magnitude) resulted in proportionately higher levels of recovery.

The first column describes three typical miniplasmids that are used as vectors. Both RepFIC and RepFIB depend on synthesis of an initiator protein. The efficacy of cysteine for RepFIC is greater than that for RepFIB and does not apply to pUC-18 or 19. The pUC plasmids do not code for initiator proteins and depend on cellular factors for initiation. The reasons for the efficacy of using cysteine in the recovery of cells transformed with RepFIC derivatives is well explained below. RepFIC is a stable and convenient plasmid, with few restriction sties in its replication region. Thus, to create a commercial kit, one can insert a polylinker with a variety of restriction sites. The restriction sites are then used for inserting DNA fragments that one wishes to clone.

Transformants recovered in the presence of cysteine continue to require cysteine for a number of generations, generally about 20. Cysteine, however, is quite poisonous to $E.$ $coli$ and, therefore, after transformation, it is best to allow the cells to grow overnight in the presence of glutathione. Glutathione acts as a "slower" source of cysteine. After the 20 or so generations of growth in the presence of glutathione, the cells no longer require additional supplements. The growth of large numbers of clones by transfer into the appropriate media can easily be automated by inoculating microtiter plates.

Methylation is Limiting for Initiatinq Replication

After obtaining the above described efficient recovery of transformants in electroporation experiments, DNA was then used in a state similar to the product that is in fact used in cloning experiments. In molecular cloning the vector and the fragment to be cloned are both treated with restriction enzymes, purified and then ligated, again by enzymatic reaction. The ligated product is again purified and concentrated by precipitation. This results in a purified sample that probably does not have much peptide material associated with it. When similarly purified material was used in the above described and improved transformations, cysteine no longer helped in the recovery of transformants.

Normally purified DNA frequently still is associated with methyltransferases. To determine if the situation could be helped by stimulating the formation of the methyl donor that is used by the methyltransferases, a compound was added that is known to be a co-activator of a series of reactions that result in the synthesis of the methyl donor S-adenosylmethionine. [Schell, 1993, #316]. Addition of the co-activator completely restored the efficient recovery of transformants [Maas 2000 #188]. This indicates that homocysteine induces the biosynthesis of the dam-methyltransferase (in the case of *E. coli*) as well as the biosynthesis of S-adenosylmethionine.

Using a package of supplements (methylation care package) immediately following electroporation and during selection, the effective recovery was totally restored for highly purified transforming DNA. The package consists of homocysteine, ferrous sulfate, and magnesium sulfate. Using the package in combination with glutathione gave the highest frequencies of transformation, although not adding glutathione did not decrease the order of magnitude obtained when all of the supplements were added.

The results obtained with highly purified and partially purified DNAs are illustrated in Table 2.

The Importance of Plasmid Associated Peptides in Transformation

There was evidence that the plasmid DNA used in transformations, regardless of how extensively the bound peptide material had been dissociated, still had an intercalated peptide. In order to destroy the peptide, plasmid preparations were treated with the protease preparation Pronase (Sigma). The Pronase-treated plasma used in transformations required both the cysteine source glutathione and the methylation factors absolutely for efficient recovery. This is illustrated in the results shown in Table 3.

TABLE 3

Transformation of plasmid *DNA isolated from a lon- host: the effect of pronase treatment prior to transformation

| DNA treated with pronase | Selection supplement added | | Number of transformants |
|---|---|---|---|
| | Glutathione | Methylation | |
| 1. no | no | yes | $0.6 \times 10^9$ |
| 2. no | yes | yes | $1.02 \times 10^9$ |
| 3. yes | no | yes | $1.52 \times 10^4$ |
| 4. yes | yes | yes | $2.12 \times 10^9$ |

*Approximately 50 f-moles DNA were used per transformation.

Table 4 shows the effect of heat shock after transformation

TABLE 2

Transformation of scL and scH RepFIC plasmid DNAs into C600

| Incoming plasmid DNA | DNA input (f-moles) | *Care package added | Selection supplement added | Number of transformants | #DNA conformation transformants |
|---|---|---|---|---|---|
| 1. scL | 10 | no | none | 0 | — |
| 2. scL | 10 | no | cysteine | 0 | — |
| 3. scL | 10 | no | glutathione | $2 \times 10^8$ | scL |
| 4. IVS, scL | 20 | no | glutathione | $10^4$ | scL |
| 5. ivs, scL | 20 | yes | glutathione | $2 \times 10^9$ | scH |
| 6. scH | 50–60 | yes/no | none | $\approx 2 \times 10^4$ | scH |
| 7. ivs, scH | 50–60 | no | none | $6.4 \times 10^4$ | scH |
| 8. ivs, scH | 50–60 | yes | none/ glutathione | $1.2 \times 10^{10}$ | scL | scL and scH DNAs are plasmids of different helical densities. The abbreviation ivs indicates highly purified plasmid DNA. The plasmid was prepared from at least 10 independent isolates. The results were invariably uniform.
Rows that are grouped within solid grid lines represent experiments carried out contemporaneously with a single batch of competence cells.

and before selection on the transformation of different plasmids into a C600 host.

TABLE 4

Effect of Heat Shock after transformation and before selection on the transformation of different plasmids into a C600 host

| Plasmid transformed | Dilution used for counting | Number of transformants | Number of transformants per µg DNA | % Improvement with HS |
|---|---|---|---|---|
| # RepFIC | | | | |
| no HS | $10^4$ | 674 | $2.7 \times 10^9$ | |
| with HS | $10^4$ | 1008 | $4.0 \times 10^9$ | 33 |

TABLE 4-continued

Effect of Heat Shock after transformation and before selection on the transformation of different plasmids into a C600 host

| Plasmid transformed | Dilution used for counting | Number of transformants | Number of transformants per μg DNA | % Improvement with HS |
|---|---|---|---|---|
| # RepFIB | | | | |
| no HS | $10^4$ | 426 | $1.7 \times 10^9$ | |
| with HS | $10^4$ | 411 | $1.6 \times 10^9$ | none |
| pUC 18 | | | | |
| no HS | $10^2$ | 209 | $8.4 \times 10^6$ | |
| with HS | $10^2$ | 229 | $9.2 \times 10^6$ | *10 |

Transformants were selected in rich media with added cysteine
*Probably not significant Transformation experiments described herein demonstrate that the mechanical and artificial transfer of plasmid DNA into E. coli by electroporation is an extremely efficient process, and all entering plasmid DNA can be recovered. There are a number of factors, however, that limit the establishment of the transferred plasmid DNA as a replicating unit. One of these factors in the case of the replicon RepFIC is the availability of cysteine. In the absence of added cysteine, the transformation frequency is low, while in the presence of added cysteine it is highly enhanced. Transformants recovered in the presence of cysteine contain plasmid that reveals unexpected features in its mode of maintenance. This altered type of maintenance was stable and initially difficult to reverse. Furthermore, the altered plasmid could be isolated and retransferred, and it retained the altered mode of maintenance.

To use a computer analogy, since the sequence was not altered, the "hardware" remained unchanged. However, the genetic material of the plasmid was physically distinguishable from the native form and functioned differently i.e., the "software" had been modified. Altered software has been described as "imprinting" in eukaryotes. For the first time the occurrence of altered gene function or imprinting of a plasmid replication intermediate has been described for a laboratory strain of E. coli. The stability of the altered imprinted DNA, a state that the present inventors were eventually able to change, made is possible to analyze the software. Furthermore, the simplicity of isolating the plasmid in the altered mode of maintenance and its size (5 kg of which 3 kb are replication genes) greatly facilitated the use of simple analytical tools.

Using these tools it was demonstrated that the imprinted intermediate is maintained in a helical state of diminished linking number. Additionally, it was fully modified at frequent purine sites other than the canonical sites for dam-methylation (the $N^6$ position of adenine, Hattman et al., 1978). The modification is nevertheless shown to be dependent upon the dam-methyltransferase.

It quickly became apparent that some of the software consisted of peptides associated with the entering DNA at the time of transformation. One aspect of the co-transmission of plasmid-associated peptides was that their removal prior to transformation could lead to changes in the type of maintenance of the imprinted intermediate. Imprinting of the intermediate in lon hosts suggested that Lon-protease plays a role in each round of replication.

The picture that emerged from these studies is that the actual duplication of genomes is a defined process within a cyclical sequence of events. The results suggest that stimulation of pre-replicative processes on the one hand, or interference with post-replicative procession the other, may result in the accumulation of plasmid DNA in an activated pre-replicative site. This is DNA of diminished helical density which possibly resembles "Z-DNA" as has previously been generated in vitro (Wang et al., 1979). The biological significance of a form other than native "B-DNA" is demonstrated in the experiments described below.

Cysteine is Limiting After Transformation

The frequency of transformation of RepFIC miniplasmids in E. coli tends to be low when compared to (iteron) plasmids of the mini-F type. The explanation for this has not been evident, for RepFIC is maintained at a copy level somewhat higher (about 5 times) than that of the iteron plasmids. While trying to optimize transformation in order to study the subsequent steps, it was noted that the number of transformants on the selective plates decreased less than proportionately for the usual ten-fold dilutions. For instance, a 10-fold dilution of a suspension that produced 200 colonies per plate would consistently result in 60–70 colonies per plate. This suggested that a nutrient was limiting the outgrowth of transformants on the plate with 200 colonies. As the media used were tryptone-yeast extract supplemented with glucose and the selective drug, and proteins contain low levels of cysteine, it was hypothesized that cysteine could be limiting. In the first experiment designed to test this idea, additional magnesium sulfate or L-cysteine was added to the selective medium, and unexpectedly there was an increase of the order to $10^3$-fold in the number of transformants in the presence of additional cysteine. Magnesium sulfate had no effect. The optimal concentration of cysteine was 400 micrograms per ml. When the cysteine concentration was less than optimal, the transformant colonies were small and somewhat transparent.

The precautions that need to be taken to make solutions of cysteine, its derivatives or its precursor N-acetylcysteine are described below. The results of a typical experiment are shown in Table 1, rows 1 and 2. For the first time in the experience of the inventors, the transformation numbers became totally reproducible. The transformant colonies obtained, once precautions were taken to keep all of the cysteine in the reduced state, were normal in size and appearance. The transformation of two other plasmids is shown for comparison purposes. A pUC18 derivative that has a partial and non-functional RepFIC insert showed no increase in the number of transformants with the addition of cysteine, presumably because plasmid replication did not require the de novo synthesis of an initiator protein. RepFIC, the second unrelated control plasma used, is a deregulated iteron-type (like mini-F) variant that makes 4 to 8 times the normal amounts of plasmid DNA (Maas et al., 1989). It requires a plasmid-encoded initiator, and, as shown in Table 1, responds to the addition of cysteine with a 500-fold increase int eh number of transformants. The two control plasmids, rows 3, 4, 5 and 6) demonstrate that cysteine is not freely available in the cell and can be limiting. For instance, when new genetic material is introduced into the cell, the requirements for duplicating this material could create stress. The stress could be aggravated when a protein needs to be synthesized de novo (rows 5 and 6). Electroporation per se does not result in a cysteine requirement.

A number of supplements to rich media were tried as substitutes for the L-cysteine effect in RepFIC transformations: L-methionine, L-arginine, L0cysteic acid, -acetyl-D, L-cysteine, glutathione, and L-cystine. None of these was effective except for glutathione. Glutathione (glutamyl-cysteinylglycine) was used at a concentration of 300 micrograms per ml, as compared to 400 micrograms cysteine per ml, with the expectation that the lesser availability of cysteine would permit activation of the Cys regulon. The number of colonies obtained was the same as with cysteine, but they were very tiny and transparent, as were the colonies obtained with less than optimal amounts of cystein supplement. N0acetyl-D,L-cysteine was tried because the L-isomer, a cysteine precursor, is a known coinducer of the Cys regulon. However it is possible that it is not transported into the cell, or there may be another factor which limits the synthesis of cysteine.

The failure of cystine to substitute for cysteine was taken as an indication that cysteine itself, and not its oxidized product, is required. Thus it was concluded that cysteine is required very specifically for the synthesis of one or more plasmid encoded activators. Addition of cysteine before selection had no effect, and thus appears to play no part in the transformation process proper. However, if the initiation of replication depends on the principal initiator and possibly some of its accessories, then presumably replication will not initiate until they are synthesized. The magnitude of the increase suggests that the biosynthesis of the initiators is an integral part of the initial step in replication.

The organization of the replicon RepFIC (Picken et al., 1987; Saadi et al, 1987), identical to the well-studied replicons R1 and R100, is illustrated in FIG. 1. The elements that have been shown to be essential are the initiator RepA (Maas et al., 1991) and an origin region labeled ori (Masai et al., 1983). The three other indicated polypeptides are all expressed and presumably accessory. RepB is a regulator of one of two promoters, indicated as $P_A$ (Molin et al., 1981). The function of RepC is at present unknown (Wagner et al., 1987). UORF (24 amino acids, or Aas) and RepA (340 Aas) each contain two cysteines, and the translation of RepA is largely, although not obligatorily, coupled to that of uORF (Blomberg et al., 1992; Wu et al., 1992). Cysteine limitation could thus influence replication by limiting the synthesis of both uORF and RepA. The specific function of RepA has not been irrefutable demonstrated, although in vitro studies have shown that it may have tropoisomerase activity of the I-type. The work described herein is consistent with the initiator protein RepA having a topological function.

The coupled translation of uORF-RepA (despite braod differences in the RepA sequence of the different E. coli replicons) involves a shift at 23.cys or UORF to 1.met of RepA, as shown in FIG. 1. The coding sequence at the frameshift, absolutely conserved, it <u>TGTG</u>. The first three nucleotides code for cysteine and the second, third and fourth nucleotides proved the less common methionine starting codon (GTG) by a −2 shift. The enhancement created by an unlimited supply of cysteine during selection of transformants is very large, suggesting that the synthesis of the initiators is both crucial for initiation, and highly dependent on an adequate supply of cysteine. The enhancement could reflect cysteine-dependent, slow synthesis of the uORF leader peptide, ribosomal pausing at the frameshift site and an ineffective ribosomal binding site preceding the first amino acid of RepA. The increased production of RepA could insure initiation of replication and, in addition, the enhanced synthesis of uORF may favor the initiation reaction.

It quickly became apparent that an altered state of plasmid maintenance had been established, presumably by the increased production of uORF and RepA. As might be expected of a cycle composed of several steps where regulation is positive and the rate of one step (progress of the replication fork) is relatively invariant, stimulation of pre-replicative steps or interference with post-replicative events could result in the accumulation of an intermediate complex. Analyzing how the accumulation is established and how it is refreshed identified some of the factors that affect regulation of initiation and post-replicative processing.

Cysteine-Recovered Transformants Grow as Snakes

Single colonies that were normal in appearance, selected after transformation of C600 hosts in the presence of cysteine (Table 1, row 1) were resuspended in liquid medium. Aliquots were streaked onto spectinomycin-containing plates and spectinomycin plates with the following additives: cysteine, cystine, or glutathione. The transformants only grew on the glutathione-supplemented plates. It was concluded that transformants selected in the presence of cysteine remained phenotypically Cys for a period of time. They appear to be, however, poisoned by an excessive supply of cysteine. Cysteine metabolism adjusts slowly to environmental changes, and cysteine can become poisonous at excessive concentrations. Transformants selected in the presence of cysteine and grown overnight in rich medium supplemented with glutathione no longer required additional supplements. These observations suggest that once the translation of RepA is stimulated and increased, replication initiates in an alternative state that requires increased availability of cysteine, and therefore of the initiators. After an undetermined number of cell divisions, the cellular metabolism adjusts to the changes and the cultures are no longer dependent on glutathione supplements.

Figure 2A:
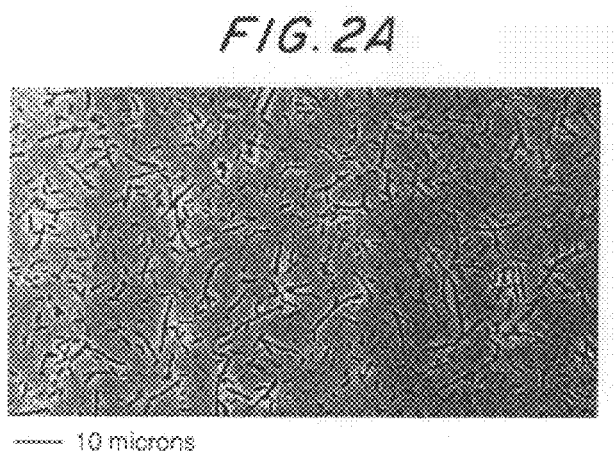
FIG. 2A shows "snake" forms of E. coli hosts containing scL RepFIC miniplasmid. C600 was transformed with RepFIC under conditions of cysteine-enhanced selection. Cells were viewed with a phase-contrast microscope during the exponential phase of growth.

When the glutathione-grown cells were inoculated into unsupplemented and rich fresh medium, the cellular mass (as measured by optical density) increased with a lengthened doubling time of 60 rather than the usual 42 minutes. Samples form the logarithmic cultures examined under the phase microscope consisted of typical E. coli "snakes", as shown in FIG. 2A. The snake phenotype was maintained indefinitely to varying degrees of lengthening of the cells in a periodic manner. During exponential growth, the cells lengthened into snakes, and as the optical density of the culture leveled off in stationary phase, the cells began to divide. Normal plasmid-containing stocks were unaffected by growth in cysteine- or glutathione-supplemented media. Thus, the shift in phenotype to snakes occurred during transformation.

Figure 2B:
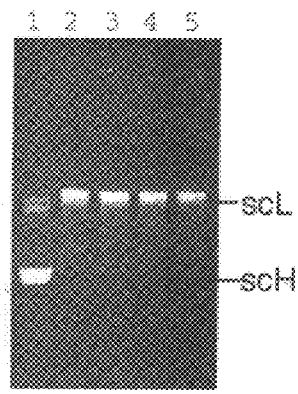
FIG. 2B shows electrophoretic mobility of scL and scH (highly supercoiled) RepFIC. In Lane 1, plasmid prepared from a normal C600 stock grown overnight with methylation care package (cf. Experimental procedures). Lane 2 is plasmid prepared from a transformant after cysteine-enhanced selection. Lane 3, transformant used in lane 2 was successively inoculated into fresh medium six times. Lane 4, plasmid prepared from a transformant in a lon host. Lane 5, transformant used in lane 4 was successively inoculated into fresh medium six times.
Figure 2C:
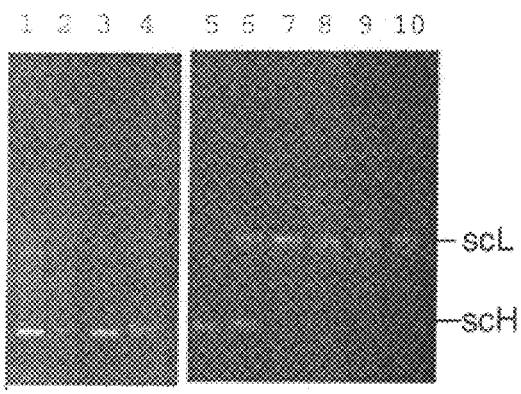
FIG. 2C shows information transfer in plasmid transformation by co-transmitted protein and by the DNA conformation. In lanes 1–4, salt-stripped plasmid preparations from single colony isolates transformed with salt-stripped scL DNA as shown in FIG. 2B, lane 3. In lane 5, preparation of RepFIC miniplasmid from an exponentially growing culture. Lane 6, same plasmid preparation was salt stripped. Lanes 7–10, salt-stripped plasmid preparations from single colony isolates transformed with DNA as shown in FIG. 2B.

Transformed E. coli Snakes Contain Plasmid of Altered Mobility in Agarose Gel Electrophoresis Plasmid DNA isolated from the cysteine-recovered, glutathione-grown transformants could be distinguished from native supercoiled plasmid DNA by agarose gel electrophoresis in the absence of intercalating agents, as shown in FIG. 2B. Plasmid isolated from the snakes has a reduced mobility in 0.8% agarose gels similar but not identical to that of nicked-relaxed plasmid or plasmid dimers. The reduced electrophoretic mobility indicates a lower linking number (Kornberg and Baker, 1992). Plasmid obtained from snakes does not penetrate 0.8% gels unless it is first treated with salt, as shown in FIG. 2C, lanes 5 and 6. Moreover, even after salt treatment, it does not penetrate gels that have been pre-stained with ethidium bromide, even if ethidium bromide is added to the samples prior to loading. It is show infra that the DNA is chemically modified in addition to its lower linking number.

The preparations were examined by electron microscopy. Plasmid preparations from normal stocks and preparations from the snakes were identical and typically supercoiled, cf. FIG. 3 for electron microscopy pictures. In each preparation there was an occasional (about 5%) open circular plasmid. These were precisely alike in the two preparations and were not dimers. About 30–500 plasmid molecules were examined in each preparation, and not a single dimer was detected. The preparations were UV irradiated, and in both cases identical open circular forms were obtained. Thus, in both cases the plasmid is circular and supercoiled. It should be noted that there is much visible DNA breakdown in the background of one spread, shown in FIG. 3B.

Electron microscope spreads are not necessarily informative about the degree of supercoiling, but the unequivocally demonstrate where plasmid preparations are supercoiled or open-circular. Agarose gel electrophoresis, on the other hand, indicates linking number characteristics of supercoiled plasmids. The supercoiled nature and low linking number of plasmid DNA isolated from snakes indicates a helical structure that might resemble "Z-DNA", where the number of bases per turn of the helix is 12 rather than 10.5 in B-DNA. These two distinguishable DNAs are also referred to as scH (higher) and scL (lower) for their higher and lower linking number.

When plasmid was purified using Qiagen Plasmid Mini kits, all RepFIC preparations were found to contain some scL DNA, with the amount varying depending on the stage of growth of the culture. The amount in exponentially growing cultures was found to be less than 5% of the total plasmid, and as the cultures approached stationary phase it was found to increase to approximately 70%. If stationary-phase cultures were diluted 1:20 into fresh medium, within two cell divisions scL plasmid accounted for less than 5% of the total plasmid.

The phenotypic nature of the change in maintenance was confirmed by sequencing several variants. As there were no mutations, the change was heritable but phenotypic, and could be thought of as imprinted.

Metabolic conditions can thus be manipulated at the time of transformation in a manner that established plasmid maintenance in the scL mode. The first attempts to reverse scL maintenance by varying the growth conditions or by the action of supplements were not successful, although the snake phenotype could be relieved by adding iron salts or magnesium salts. Thus, the snake phenotype was not the direct result of the DNA alteration, and suggested that the accumulated product might be inhibiting cell division.

Transformation of the scL Plasmid

To ascertain that the scL phenotype was heritable under all circumstances and viable, scL DNA was transferred into C600 by electroporation. Selection of transformants was carried out without additional supplements or in the presence of cysteine or glutathione. The results are summarized in Table 2, rows 1, 2, and 3, and they demonstrate that scL plasmid DNA is efficiently recovered in transformations, but only with glutathione supplements (row 3). Thus, although an additional source of cysteine is still required under the conditions of this transformation, cysteine becomes toxic at the concentration that was previously used. Thus suggests that when the plasmid enters competent cells in the scL form, the requirement for cysteine is diminished but not eliminated.

Properties of scL DNA

RepFIC scL plasmid does not precipitate in ethanol-salt unless it is in vitro salt-stripped first. Thus, it is probably "overloaded" with non-covalently bound products. It partitions into phenol-chloroform even after in vitro salt-stripping. The solubility in phenol-chloroform after extensive salt treatment is an indication that RepFIC scL DNA might still has peptide material associated therewith.

This associated peptide material may be the 24 amino acid peptide uORF, and it may intercalate the DNA. If the intercalator is indeed the leader peptide of the initiator RepA (FIG. 1), then it contains one tryptophan at position 22, and thus would be expected to fluoresce in the blue-green range under UV excitation. When repFIC plasmid is loaded onto agarose gels and allowed to migrate eletrophoretically for about 15 minutes at 14 volts per cm, fluorescence can be clearly seen in the well region. The fluorescence can be photographed on a UV transilluminator using a Kodak #11 Wratten gelatin filter, which transmits with a peak at 570–580 nm. As the plasmid is allowed to migrate in Tris-borate buffer, the fluorescence remains in the well area while the plasmid DNA migrates to its characteristic scL or scH positions, as shown in FIG. 2B. Thus, the intercalated or associated peptide material is dissociated from the DNA by the applied current and does no affect the electrophoretic mobility of the plasmid.

ScL DNA is Fully Methylated

In *E. coli*, methylation sites shuttle between the fully methylated state (prior to replication) and the hemimethylated state (post-replicatively). DpnI, an enzyme isolated from Pneumococcus, is the only known restriction enzyme that distinguishes in vitro full 2-strand methylation on the one hand from hemimethylation and the unmethylated state on the other. DpnI restriction has only been demonstrated with fully methylated GATC palindromes. Hydrolysis occurs at the symmetrical $5'\text{-}^{me}\text{A-T}$ sequence. The isochizomeric enzymes MboI and DpnII restart the sequence GATC efficiently when neither strand is methylated.

RepFIC has notably infrequent GATC sites (none in the origin), namely a total of three in 3 kilobases of sequence, clustered in the promoter region. The 2 kb drug marker omega, used in cloning RepFIC, has 19 GATC sites. Restriction at the omega sites, which are not evenly distributed, results in a fragment ladder ranging from 10 to 550 base pairs. Restriction at all plasmid GATC sequences predicts a 2.5 kb fragment in the replicon, the only one of significant size. DpnI restriction of scH plasmid preparations results in the expected 2.5 kb fragment and no other fragments of significant size. Thus, all GATC sites are detected in the fully methylated state, including re-methylation after duplication.

Previous work conducted to assess methylation of dam sites in the replicon suggested that in mixed preparations of scH and scL plasmid, the latter might be modified with altered specificity. The imprinted scL form gave a unique opportunity to determine the validity of these unexpected observations.

Differences in susceptibility to piperidine of scL DNA and scH DNA were thus tested as follows: The differently conformed DNAs were treated with 1M piperidine at 86° C. for different lengths of time. The results demonstrate that scL DNA is extensively degraded by piperidine within seven minutes, while scH DNA, although changed, was still amply discernible after 30 minutes. If the specificity of piperidine hydrolysis is the same as had been demonstrated in the G-reaction of Maxam-Gilbert sequencing, then the present results argue that the methylated loci are at Gs.

Figure 4A:
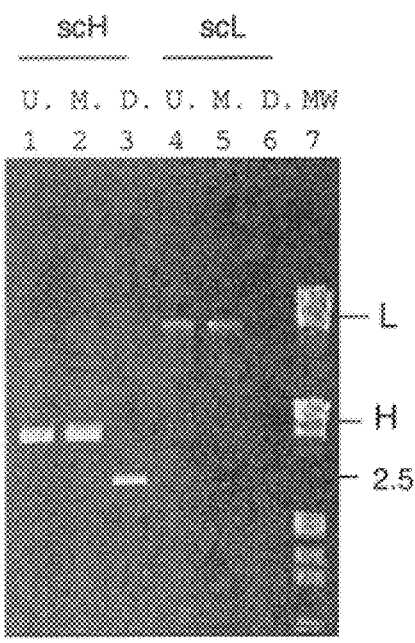
FIGS. 4A–4E show differences in methylation as demonstrated by enzymatic restriction and chemical treatment of scH and scL DNA, respectively.
Figure 4B:
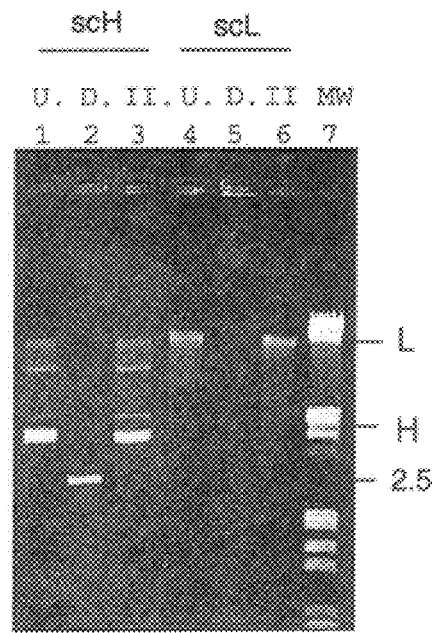
Figure 4C:
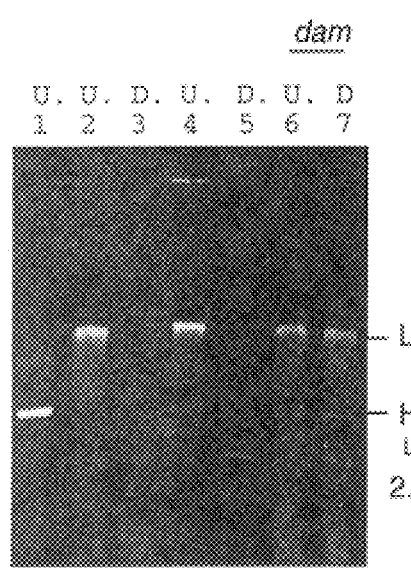

DpnI restricts GATC sites rapidly only when both strands are methylated. DpnI restriction of scH plasmid DNA results in the expected RepFIC fragment of 2.5 kb. Using the amount of enzyme recommended by New England BioLabs, the reaction was always complete within 30 minutes, indicating that most or all of the GATC sequences are fully methylated (FIG. 4A, lane 3). The methylation of GATC sites was confirmed by the absence of restriction with MboI, an enzyme that is blocked by methylation of adenines in GATC sequences (FIG. 4A, lanes 2 and 5). This reaction, however, does not distinguish between full and hemimethylation, since methylation of one strand blocks the activity of the enzyme.

If scL DNA is a precursor of replication, its GATC sites should also be fully methylated. If it is a post-replicative intermediate that is not remethylated, then it should be hemimethylated. To explore this point scL plasmid was digested with DpnI. Unexpectedly, DpnI restriction of scL plasmid results in the degradation of the 2.5 kb fragment (FIG. 4A, lane 6), which contains no GATC sequences. The DpnI treatment of scL DNA was carried out as a time course. DpnI digestion was complete within 15 minutes, and this confirmed that the 2.5 fragment had been cut. An unresolved broad band with an electrophoretic mobility somewhat greater than that of the bromophenol blue marker dye was independent of the time of digestion. These findings suggest that DpnI restriction, although apparently still methylation-dependent, is not exclusively GATC specific as had been previously assumed. Resistance to restriction by the isoschizomeric enzymes MboI or DpnII of both scH and scL plasmid confirms the methylation of all GATC sequences. The unexpected DpnI restriction patter was confirmed several times with independently prepared scL plasmid samples and different commercial batches of DpnI. The experiments were conducted with independently prepared plasmid samples and different batches of all enzymes.

The different restriction patterns of scL and scH plasmids, obtained with single batches of DpnI in each experimental, preclude contamination of the commercial DpnI preparations with a non-specific nuclease. The absence of restriction of either type of plasmid when incubated with DpnI burre, precludes the contamination of scL plasmid preparations with non-specific nuclease activities.

Is the Altered Pattern of DpnI Restriction Related to Methylation?

Mixtures of scH and scL plasmid, or mostly scL plasmid, were prepared from a dam host and a dcm host, respectively. In each case the mutant host lacked the corresponding *E. coli* methyltransferase. The samples were then restricted with DpnI. When plasmid was isolated from the dam host, and only when isolated from this host, scL plasmid was fully resistant to DpnI restriction, indicating that there is no DpnI restriction of scL plasmid when the latter has not been methylated by dam-methyltransferase. Restriction of plasmid DNA from this host with the enzymes MboI or DpnII resulted in the diagnostic 2.5 kb fragment. This evidence supports the established hypothesis that the DpnI restriction depends on full methylation, and also suggests that dam-methyltransferase can methylate DNA sequences different from GATC. The scL structure, however, is not dependent on methylation.

The Dam-methyltransferase Reaction in Vitro

Figure 4D:
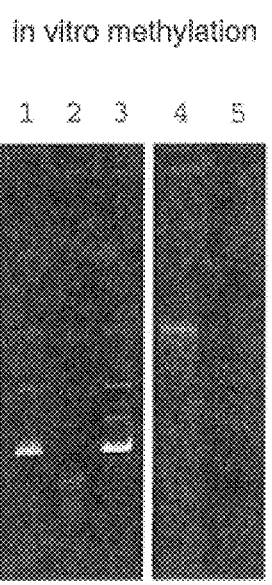
Figure 4E:
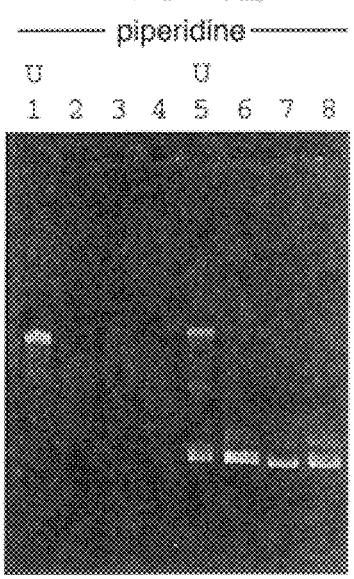

In order to confirm that the methylation reaction is different for the DNAs of different helical density, the methylation reaction was carried out in vitro. A preparation of mostly scL DNA isolated from a dam host, and a preparation of mostly scH DNA isolated from the same host, were treated with commercial *E. coli* dam-methyltransferase. The in vitro-treated plasmids were then restricted with DpnI, since this The results indicate that in vitro methylation by dam-methyltransferase results in the same pattern or restriction as obtained with in vivo methylated scL and scH plasmids respectively, as shown in FIG. 4D.

In numerous ladders obtained when the plasmid was copied by repeated primer extensions (Maas and Wang, 1997; Maas et al., 1997), there were unexplained G signals, as if the polymerase were stalling at the G sites. In retrospect, there could have been methylated Gs.

Chemical Detection of Methylated Nucleotide Bases

Modification of G's by methylation at the N7 position, as is obtained with the reagent DMS, renders bonds in the sugar-phosphate backbone located at the modified G's susceptible to hydrolysis by piperidine. This reaction is used to locate G's in Maxam-Gilbert sequencing (Maxam and Gilbert, 1980).

ScL DNA is Sensitive to Piperidine Degradation

Piperidine degradation of the DNA sugar-phosphate backbone after in vitro modification of purine-nucleoside sites is used in Maxam-Gilbert sequencing. Presumably methylation of the purine rings exposes the backbone and sensitizer the DNA molecules to hydrolytic degradation. *Dam methylation of scL DNA results in a higher level of methylation of this DNA as compared to scH DNA, where the *dam sites are presumably hemimethylated.

The sensitivity to piperidine degradation appears to correlate well with methylation, as demonstrated by restriction with DpnI. Piperidine could prove to be a useful reagent for investigating the level of methylation in cases wherein the methylation enzyme differs from dam-methyltransferase.

In Vitro Salt-Stripping of Imprinted scL Plasmid DNA

Evidence has been presented for the stable maintenance of the scL conformation. It has been interpreted as the "imprinting" of a maintenance phenotype. Under these conditions, the plasmid is fully methylated at non-canonical sequences. The altered plasmid can be transferred by transformation and both its altered conformation and methylation characteristics are retained, as shown in Table 2, row 3. Thus, the conformation of the DNA and its methylation pattern are retained during the transformation process.

In order to identify the contribution of co-transmitted molecules that are easily removed, scL DNA was in vitro salt-stripped before being transformed. The results are shown in Table 2, rows 4 and 5. Row 4, when compared to row 3, shows that salt treatment strips scL DNA of a critical component, because the addition of glutathione is no longer sufficient for the efficient recovery of transformants. Plasmid preparations are associated with several proteins, of about 32 kda in size, which could be the dam-methyltransferase (GenBank accession no. J01600). Therefore, it is possible that the dam-methyltransferase is one significant component removed by the salt treatment.

The methylation reaction per se could have become limiting as a result of the removal of methyltransferase, and activation of the biosynthesis of S-adenosylmethionine (SAM), the methyl donor in the methylation reaction, could help overcome low enzyme levels in the cell. Homocysteine is a known co-inducer of the MetR regulon (Schell, 1993), and thus activates the synthesis of SAM (Palmer and Marinus, 1994). Thus, an empirically devised package of supplements was added, referred to as a "methylation care package." This package consisted of $Fe^{++}$, $Mg^{++}$, and Homocysteine. It was added after DNA entry and to the selective plates. The high and reproducible difference obtained in the recovery of transformants as shown in Table 2, row 5, the latter having been increased by a factor of $2\times10^5$ fold, justifies the "care package" nomenclature. Homocysteine rescued the transforming ability of salt-stripped plasmid, suggesting that the removed component is dam-methyltransferase. Additionally, the plasmid was restored to scH→scL→scH maintenance, as shown in Table 2. For purposes of the present application, the restoration of normal plasmid maintenance will be referred to as "rebooting", the same word used to described the function of Lon after each round of DNA duplication.

A Rebooting Role for Lon-Protease

As described above, scL maintenance was so far established during transformation of normal hosts under specific conditions. The conditions involved adding the amino acid cysteine immediately after electroporation and during selection of transformants. Imprinting of the scL phenotype under these conditions suggested that cysteine was limiting for the synthesis of a protein that causes the scH→scL shift. If the shift is a reaction that occurs every time that plasmid replication initiates after cell division, then there must be a reaction that results in the back-shift every time that the plasmid DNA has duplicated. One possibility is that a protease removes the protein(s) responsible for the shift and the dam-methyltransferase at the same time, removal of the latter resulting in full origin methylation only after cell division and the shift to scL.

Lon appeared to be a good candidate for removal function, based on a feature of the replicon sequence described below. A protein of about 90 kda (the size of Lon) is one of the proteins associated with plasmid preparations, and furthermore, evidence for the removal of Ccrm methyltransferase by Lon-protease has been documented in *Caulobacter crescentus* (Stephens et al, 1996).

The following sequence in the RepFIC replicon, starting at nucleotide 647, ending at nucleotide 682, and underlined below, has 50% homology to abn HIV enhancer sequence (PETS), previously shown to bind *E. coli* lon (Fu et al., 1997):

clears plasmid doublets of associated proteins after DNA synthesis is complete.

The scL→scH Back-Shift

The scL->scH transition could be expected to occur after plasmid-associated proteins are removed by Lon-protease, as suggested above. The Lon step requires ATP. The actual transition could be a gyrase-like reaction, and probably requires ATP and $Mg^{++}$. ATP biosynthesis is down-regulated by catabolite repression, and potentially could be stimulated by growth in the absence of glucose. Accordingly, conditions of growth were explored for obtaining the back-shift, using glycerol as a carbon source. The results, demonstrate that the back-shift can be obtained by altering the growth conditions. The scL phenotype is retained in the lon host under the same conditions in which it is removed in the wild-type host, suggesting that absence of Lon stabilizes the scL phenotype.

Lowering DNA Helical Density

It has been shown previously that priming replication RepFIC occurs by the Rnase H processing of a transcript (Maas and Wang, 1997). The processing, which takes place at the site labeled ssr requires transcription of the repA gene as well as transcription of part of the adjoining region (Maas et al., 1991; Maas and Wang, 1997; Masai and Arai, 1988; Masai et al., 1983). The cloned RepFIC replicon can only support the replication of a pUC vector in polA mutant hosts when RepA, a 39 kda protein, is present (Maas et al., 1991). Additionally, the number of RepFIC initiations is increased by the presence of RepA on a separate plasmid (Maas and Wang, 1997). For the experiments published in Massa and Wang, 1997, the host had been transformed with both RepFIC and a pBR vector that over-expressed RepA. Plasmid preparations were isolated during exponential growth and at the same optical density from the same host containing (i) pBR-RepA, (ii) RepFIC ad (iii) RepFIC and pBR-RepA. They demonstrate that in vivo, under conditions in which the concentration of scL RepFIC is minimal, RepA appears to alter the helical density of RepFIC. The helical density of RepFIC was lowered to both scL and an intermediate density lower than scH. Thus, initiation of replication of RepA lowers plasmid helical density, a conclusion that is supported by the in vitro demonstration of type-I topoisomerase activity for RepA of plasmid R1.

Patterns of RepFIC Methylation During Growth of a Culture

It has been demonstrated that non-canonical sites with RepFIC become fully methylated when its conformation is altered. In order to define the position within the replicon of at least some of these sites, patterns of methylation were checked by digesting with DpnI plasmid prepared from

```
  1 GATCCAGCTATACTTGTCAGGGCGAATTCTAACTA..     (SEQ ID NO:1)
    | ||| | || |   | ||| | | || ||
647 TAGCCAACAATTCAGCTATGCGGGAGTATAGTTA 682    (SEQ ID NO:2)
```

This putative Lon binding sequence is located in the regulatory region that precedes the uORF coding sequence and thus could influence the affinity of Lon for the replication region.

RepFIC was transformed into a ion strain, *E. coli* B (naturally lon) under conditions that do not result in imprinting when wild-type hosts are transformed. Plasmid isolated from the lon hosts was scL, wherein the results are shown for deltalon-501). The scL imprint was retained after six successive transfers of one transformant colony into fresh medium. The results support the view the Lon protease cultures at different stages of growth. The methodology detected fragments larger than 100 bp. The fragments larger than 100 bop resulting from restriction at fully methylated GATC loci are predictable. Besides the 2.5 fragment within the replicon and a 330 bp fragment between the two promoters $P_{ABC}$ and $P_A$ of the replicon, coinciding with one of the five following fragments, there are five fragments that originate from the drug marker. Three fragments of approximately 400, 300 and 100 bp are not predicted, and are most likely to originate in the 12.5 kb portion of the replicon sequence, since it is this fragment that is degraded when fully methylated at non-canonical sites. This portion extends from about the −10 sequence of the promoter $P_A$ to the end of the origin. Earlier studies have shown that the transcript originating at $P_A$, or the alternative promoter $P_{ABC}$, and ending about half-way into the origin, is cut by RNase H at ssr for initial priming (Maas and Wang, 1997; Maas et al., 1997). The entire transcript thus constitutes part of the functional origin, and the non-canonical sites within the diagnostic fragment can be said to occur in the functional origin region.

Efficiency of Transformation

The frequency of transformation of *E. coli* by RepFIC miniplasmids tends to be low when compared to iteron plasmids of the mini-F type, such as RepFIB (cf. Table 1). The recovery of plasmid DNA added was less than 1% for all of the plasmids tested, in spite of the factor that an electroporator was used. The difference for the different plasmids, which was reproducible, suggested that the low recovery was not a result of plasmid entry, but rather was due to the inability of the plasmids to initiate replication consistently and equally.

RepFIC possibly requires both the synthesis of the initiator and a change to lower helical density in order to initiate replication. Since the initiator RepA has been shown to lower the helical density, it could be that following transformation a protein precursor, such as an amino acid, is limiting to the synthesis of RepA. RepA and its translationally coupled leader peptide both contain cysteine.

In the first experiment designed to test this idea, additional magnesium sulfate of L-cysteine was added after electroporation. This led to an increase in the transformation efficiency of five orders of magnitude with the addition of cysteine, while magnesium sulfate had no effect. The results of a typical experiment are shown in Table 1, rows 1 and 2. The addition of cysteine altered the transformation efficiency to become reproducible and proportionate to the amount of DNA added. The transformation of two other plasmids is shown for purposes of comparison. A pUC18 derivative that has a partial and non-functional RepFIC insert showed no increase in the number of transformants with the addition of cysteine, presumably because plasmid replication did not require the de novo synthesis of a cysteine-requiring protein. RepFIB, the second unrelated control plasmid used, is a deregulated iteron-type variant, like mini-F, that makes four to eight times the normal amounts of plasmid DNA (Maas et al., 1989). RepFIB replication requires a plasmid-encoded protein that contains cysteine, and as shown in Table 1, responds to the addition of cysteine with a 500-fold increase in the number of transformants.

Electroporation per se does not result in a cysteine requirement, and addition of cysteine to media used to grow RepFIC-containing *E. coli* hosts, where the plasmid is established, does not alter plasmid maintenance. Addition of cysteine before selection had no effect, and thus appears to play no part in the transformation process proper. These results indicate that cysteine becomes limiting at the time that plasmid replication has to initiate for the first time after transformation.

Single colonies selected after transformation of C600 hosts in the presence of cysteine (Table 1, row 1) were initially difficult to grow. They appeared to have remained phenotypically Cys for a period of about 20 generation, or one round of overnight growth. They grew best in this round of growth with glutathione supplements, and afterwards could be grown normally with no supplements. One interpretation of these findings is that the transformants still required additional cysteine, but were poisoned by an excessive supply thereof (the concentrations of glutathione supplements were equivalent to ¼ of the cysteine concentrations). It is believed that cysteine metabolism adjusts slowly to environmental changes, and cysteine can become toxic at excessive concentrations.

Plasmid isolated from both lon hosts was in the scL form, FIG. 2B, where the results are shown for delta lon-510, and remained so during six transfers, demonstrating that absence of Lon inhibits the scL→scH transition. Passage through a lon host resulted in scL plasmid that remained scL when transferred back into C600. Thus, passage through a ion host can establish the altered replicative state, implicating Lon in the removal of DNA-binding proteins.

ScL DNA in LON* Hosts

It has been shown that when RepFIC is transformed into Lon* hosts, an imprinted mode of replication can be established that appears as a Lon* phenocopy. The imprinted mode is not removed in subsequent rounds of replication. It has been said that Lon is induced by heat shock. Heat shock, however, does not restore the scH form. Assuming that Lon is indeed associated with the genome, if the number of Lon molecules per binding site is fixed, it may not be possible to increase the level of Lon-protease activity. If Lon passively paves the way for the scL→scH transition by removing DNA-binding proteins, and is kept on the genome in limited quantities as suggested above, then it should be possible to overcome inhibition of the transition in either of two ways. The accumulation of the pre-replicative intermediate could be minimized on the one hand, or the actual transition could be stimulated on the other.

Stimulating the scL→scH Transition

Figure 2D:
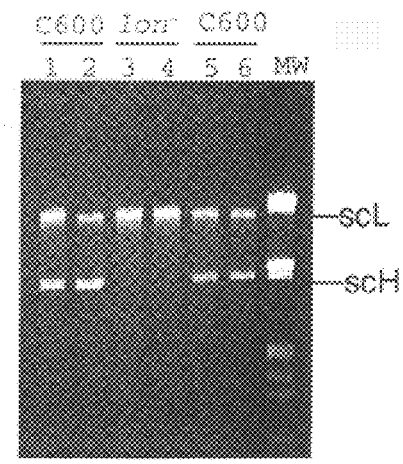
FIG. 2D shows reversal of imprinted scL plasmid to scH in vivo is lon-dependent. Strains containing the RepFIC miniplasmid were grown overnight in LB broth medium supplemented with 0.8% glycerol, homocysteine and ferrous sulfate. In lanes 1 and 2, the plasmid was non-imprinted. In lanes 3 and 4, the plasmid was isolated from a lon host. Lanes 5 and 6, the plasmid was originally imprinted (scL). In the even numbered lanes, media was additionally supplemented with 10 mM phosphate salts.

Glycerol, when used as a carbon source, avoids catabolite repression. The plasmid was prepared from the following hosts grown overnight with the supplements homocysteine and ferrous sulfate, using glycerol as a carbon source: C600 containing the non-imprinted plasmid, the lon host Δlon-510 (containing the imprinted scL plasmid), and C600 containing the imprinted scL plasmid. The results are shown in FIG. 2D. The yield of plasmid was greatly increased, from 5 to 10-fold, for both C600 and the lon host with the glycerol carbon source, thus showing that replication of the plasmid was stimulated in the absence of catabolite repression. One interpretation of the difference seen between lanes 3–4 and 5–6 is that when Lon is present (C600) and there is no catabolite repression, the post-replicative steps occur at a sufficient rate to adjust for the recovery of the final product, scH plasmid. When Lon is absent, stimulation of steps occurring after normal Lon-processing are ineffective because the substrate for these steps is insufficient.

Plasmid Maintenance in the Absence of Lon

Figure 5A:
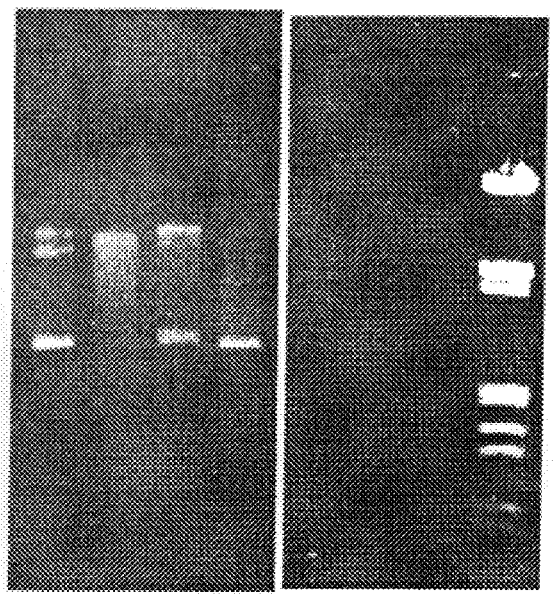
FIGS. 5A–5D illustrate ExoIII action on plasmid DNA as a model system in vitro.

The lon host Δlon-510 was ground with glycerol, which was convenient in that the snake phenotype was removed with the glycerol carbon source, and the following supplements: Homocysteine and $Fe^{++}$, homocysteine and magnesium sulfate, or no supplement. The results are presented in FIG. 5A. The only conditions of growth where the plasmid remains imprinted as scL is in the presence of homocysteine and iron (lane 2). This suggests that both homocysteine and $Fe^{++}$ promote the accumulation of the pre-replicative scL form. In all other cases there is mixture of sc forms, suggesting that even in the absence of Lon, the transition of scL to scH can occur. The methylation status of the DNAs obtained after growth of the lon host with homocysteine was checked by restriction with the enzyme DpnI, and in this case all DNAs were totally degraded within 30 minutes (FIG. 5A). Thus in the presence of Lon only scL DNA is *dam methylated, while in the absence of Lon all sc forms are *dam methylated. One possible explanation is that normally, the their presence of Lon, duplicated plasmid is not immediately remethylated because the methyltransferase is degraded. If lon is bound to DNA throughout the cell cycle, hemimethylation of low-linking number DNA probably provides the signal for the removal of DNA-associated proteins (including the dam-methyltransferase).

ExoIII: A Paradigm for Type I Topoisomerases

Imprinting of the scL plasmid conformation results form the accumulation of an intermediate of replication. In the lon host, scL imprinting leads to a lowering of the number of plasmid molecules per cell. When scL plasmid isolated from lon hosts is viewed in electron microscopy streaks, there is a lot of DNA breakdown, as shown in FIG. 3B. Thus it is hypothesized that accumulated scL DNA is preferentially processed and eventually degraded.

If there were a degradative enzyme with conformational specificity, exonuclease III (ExoIIII) could be a cognate enzyme for scL DNA. ExoIII is not necessarily processive. It was discovered as a relatively abundant exonuclease in $E.$ $coli$ by A. Kornberg and his group in the 1960s (Kornberg and Baker, 1992). Subsequently, it was shown by several groups that endoII and endoVI have endolytic activity toward apurinic or apyrimidinic DNA. Eventually it was learned that ExoIII, endoII and endoVI are one and the same enzyme (see Friedberg, 1997, for an historical account). ExoIII excises alkylated purines as well as pyrimidine dimers generated by UV damage, which effectively are small regions of distortion. Thus functionally it has been demonstrated that ExoIII falls into a class of cognate enzymes involved in repair of distorted regions.

Figure 5B:
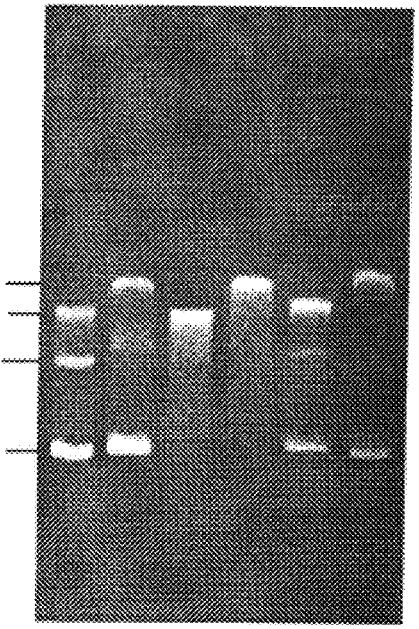

To test if is ExoIII-like enzyme might degrade accumulated distorted DNA that remains hemimethylated, different scL preparations and mixed scL-scH preparations of plasmid isolated from the ion host were treated with ExoIII (New England BioLabs) as recommended by the manufacturer in 0.66 mM $Mg^{++}$ buffer. The products were separated by agarose gel electrophoresis (FIG. 5B). Lane 1 is a preparation grown with homocysteine. There are three scDNAs: scH, scL, and a DNA of intermediate linking number (scI). The ExoIII-treated sample of lane 1 DNA (shown in lane 2) can be interpreted as follows. ExoIII reduces the linking number of scI DNA to a yet lower linking number that probably approaches zero (uppermost band). ExoIII thus acts as a type I topoisomerase. In keeping with its isomerase activity, it also lowers the linking numbers of scH and scI DNA. The lower linking conformation is probably open-circular, and its presence at a yeast higher position in the gel confirms that scL DNA is different form open-circular.

Lane 3 shows an imprinted preparation grown with homocysteine and iron. The scL DNA is fully relaxed by ExoIII to the lower linking number conformation (lane 4)_.

Lane 5 is a preparation grown in the same Ion host as the other preparations, but with homocysteine and magnesium. The linking numbers of all forms were again decreased. ExoIII thus acts as a topoisomerase of the I-type, and it preferentially relaxes scL DNA to the fully relaxed LL conformation.

Figure 5C:
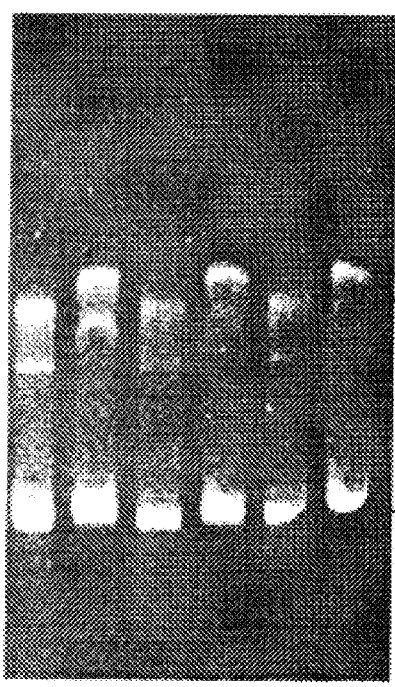

Essentially the same results were obtained with DNAs isolated from a dam strain (FIG. 5C). Thus, unexpectedly, it was discovered that not only does ExoIII preferentially convert scL to LL plasmid, possibly by nicking, but it also generally acts as a type I topoisomerase with scH DNA.

ExoIII: A Paradigm for Cognate Processing of Distorted DNA?

Careful assessment of FIGS. 5B and 5C suggests that there is plasmid breakdown over and above the lowering of the linking number. The possibility was considered that ExoIII processes DNA in two controlled steps: a topological step and a degradative step. Enzymatic nicking activities are usually related to stable active sites in enzymes and require $Mg^{++}$. A topoisomerase-like activity would be expected to be more labile. These considerations led to design of an experiment. DNA samples were treated with ExoIII in 0.66 mM $Mg^{++}$ for 30 minutes. They were inactivated at 65° C. for ten minutes and the $Mg^{++}$ concentration was increased to 12 mM. They were divided into two aliquots, fresh ExoIII was added to one, and both aliquots were incubated for an additional 45 minutes.

Figure 5D:
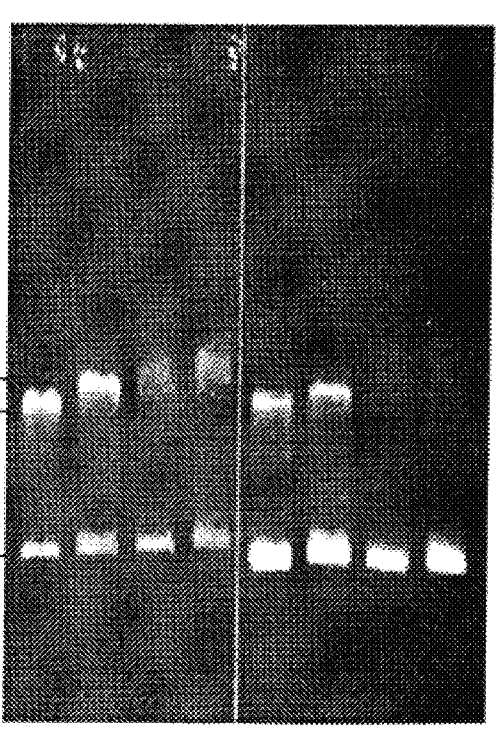

The results are shown in FIG. 5D. They demonstrate that the topoisomerase activity is inactivated at 65° C. Then, in the presence of increased concentrations of magnesium ion, the nicking activity on LL DNA is clearly evident (lanes 3 and 7). Interestingly, unmethylated LL DNA is degraded more completely than methylated LL DNA. The preference for unmethylated DNA, more likely to be the unmethylated daughter strand in vivo, probably insures that an ExoIII-like activity (or ExoIII itself) is activated after duplication, when every methylated site becomes hemimethylated.

The present inventors have previously demonstrated in vivo that the initiator protein RepA, when resident in a host, can inhibit initiation of replication of entering RepFIC miniplasmids (Maas et al., 1997). It is possible, then, that the initiator RepA not only has the topoisomerase activity of ExoIII that leads to the formation of scL DNA, but also the same degradative function.

Replication as a Cyclic Cascade

Figure 6:
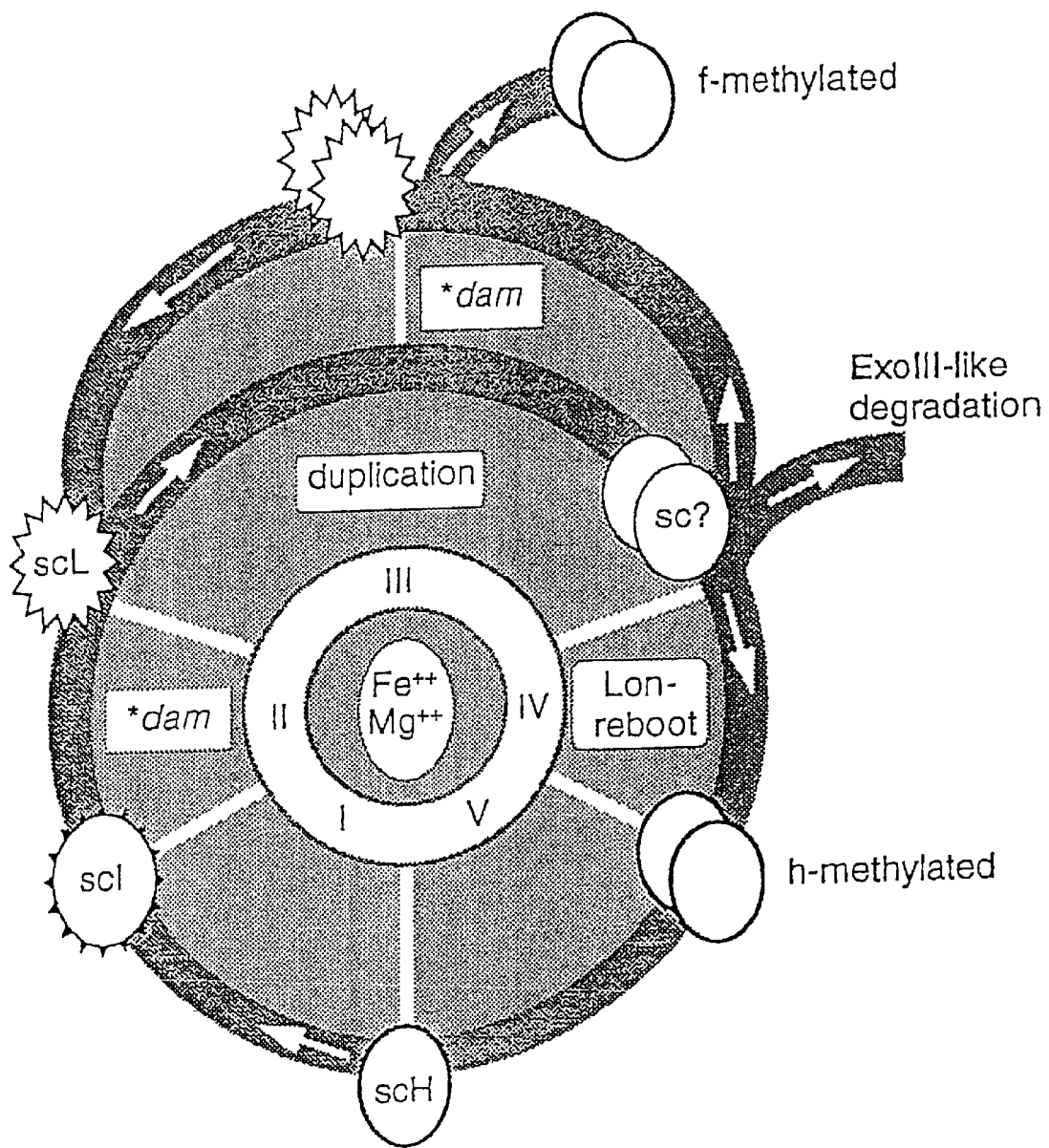
FIG. 6 shows a recognition-based cyclic cascade scheme for plasmid replication.

A cyclic cascade scheme is illustrated in FIG. 6, where the product of each step is recognized as a substrate for the next step. Replication is presumed to be an activational process, and in the scheme it consists of a series of discrete activational steps As the substrate-product molecule is too large to act as a co-regluator in the traditional sense, it would be excepted that the rate of all steps would depend on the requirement of the reaction but would otherwise be relatively invariant, whether host- or plasmid-encoded. This is supported by the fact that, although the plasmid copy number can increase, the increase is a very gradual process. For example, in transformations, RepFIC miniplasmids attain their steady copy number only after approximately 70 generations.

Many processes in the cell have evolved to preserve the quality of the genome. Hence there are proofreading enzyme, repair enzymes, etc. When disturbances in the environment lead to the accumulation of genetic material that is inappropriate, for example unrecognizable to equi-partitioning processes, there are corrective measures that restore order. One such corrective measure might be the full relaxation that is observed in vitro with the enzyme ExoIII, followed by the preferential degradation of the new and unmethylated strand. ExoIII was chosen as a model for the reactions because it is readily available commercial enzyme. However, it could be performing the same functions as the initiator RepA with its accessories, since the latter are presumably available in situ on the plasmid DNA. The validity of the analogy is supported by the fact that ExoIII could produce similar intermediates and products as were isolated in vivo, where it is more likely that they are generated by plasmid-encoded functions.

The transformation experiments described herein demonstrate that the mechanical and artificial transfer of plasmid DNA into $E.\ coli$ by electroporation is an extremely efficient process, and all entering plasmid DNA can be recovered. There are a number of factors, however, that limit the establishment of the transferred plasmid DNA as a replicating unit. One such factor in the case of the replicon RepFIC is the availability of cysteine. In the absence of added cysteine the transformation frequency is low, while in the presence of added cysteine it is highly enhanced. Transformants recovered in the presence of cysteine contain plasmid that reveals unexpected features in its mode of maintenance. This altered type of maintenance was stable and initially difficult to reverse. Furthermore, the altered plasmid could be isolated and re-transferred, and it retained the altered mode of maintenance.

Experimental Procedures

Bacterial Strains and Plasmids

The following E. coli strains were used as hosts: C600 (thi-1 thr-1 leuB6 lacY1 tonA21 supE44 mcrA), GM3819 (dam-16::Kan$^R$), GM31 F$^-$ (dcm-6), and JT4000 (Δlon-510). The host N99cI857 was used for the expression vector with cloned RepA (Maas et al., 1991). The miniplasmid used in this study was pRM3930, which consists of the RepFIC basic replicon (3 kb) and the streptomycin-spectinomycin resistance cassette Ω (2 kb). A pUC derivative plasmid, pRM4130 (3.5 kb), that has a partial RepA-ori cassette inserted in the polylinker was used as a control plasmid (Table 1). The unrelated iteron-type RepFIB miniplasmid pRM3994 (Maas et al., 1989) was used as another control plasmid.

Growth of Bacteria

Strains were grown in tryptone-yeast extract (TYE) medium (Difco) supplemented with the appropriate antibiotic for continued plasmid selection, unless specfically stated otherwise. Selective plates were made with TYE, which significantly contains 0.1% glucose. The addition of glucose to selective plates is imperative for the complete recovery of entering DNA in all hosts. Spectinomycin and amplicillin were used at 50 μg perml. All cysteine solutions of its derivatives or precursors were filter sterilized. After finding the cysteine enhancement in the efficiency of transformation (concentration used was 400 μg per ml), the following substitutes were tried: L-methionine, L-arginine, L-cysteic acid, N-acetyl-D,L-cysteine (activator of the Cys regulon), glutathione (300 μg per ml) and L-cystine. The only compound that was effective was glutathione (glutamyl-cysteinylglycine), although the transformant colonies were small and somewhat transparent. When the above supplements were added, the pH of the medium was adjusted to just below 7 (6.8–6.9) with 1N Hcl. Cysteine base was handled as follows. It was dissolved in 1N Hcl, neutralized with an equal volume of 1M Tris base prior to used and added.

Magnesium sulfate or ferrous sulfate was added at the concentrations stated below in Methylation Package when indicated.

Cultures of dam hosts containing the RepFIC miniplasmid were manipulated as described below, in order to favor maintenance of the plasmid toward scL or scH respectively. ScL DNA was prepared by growing the host overnight at 37° C. with glucose as a carbon source, and scH DNA was prepared by growing the host overnight at 30° C. with glycerol as a carbon source.

Methylation Package

The methylation package consisted of 3 supplements that were found to minimize the accumulation of diminished linking number plasmid forms. They are magnesium sulfate (20 μM), ferrous sulfate (1 μM) and homocysteine (filter sterilized, 100 μg per ml). In transformation experiments each component of the package was added (separately) as indicated to SOC medium (Bio-Rad) and the selective plates.

Preparation of sc Plasmid DNA

Standard preparations of sc plasmid were prepared by growing the cells with continued selection overnight, and when indicated in TYE medium with the supplements defined as 'methylation package'. The carbon source is specified whenever it is glycerol rather than glucose.

Preparation of DNA

Plasmid DNA was prepared with Qiagen Plasmid Mini kits (Qiagen Inc., Chatsworth, Calif.) as recommended by the manufacturer. DNA concentrations were estimated by electrophoresing the preparations in 0.8% agarose gels and staining with ethidium bromide. Electrophoretic separation was carried out in tris-borate buffer by applying 14 volts per cm, and staining was performed after electrophoretic separation, so that different native topological states could be identified.

Properties of scL DNA

RepFIC scL plasmid does not precipitate in ethanol-salt unless it is in vitro salt-stripped first. Thus it is probably 'overloaded' with non-covalently bound products. It partitions into phenol-chloroform even after in vitro salt-stripping (not shown). The solubility in phenol-chloroform after extensive salt treatment suggests that salt-stripped RepFIC scL DNA retains associated peptide material.

Associated peptide material, if tryptophan-containing, would be expected to fluoresce in the blue-green range under UV excitation. All the plasmid-encoded polypeptides contain tryptophan. When RepFIC plasmid is loaded on agarose gels and allowed to migrate electrophoretically for about 15 minutes at 14 volts per cm, fluorescence can be clearly seen as a band without staining the well region (data not shown). As the plasmid is allowed to migrate in Tris-borate buffer, the fluorescence (seen without staining) remains in the well area while the plasmid DNA (visualized by ethidium bromide staining) migrates to its characteristic scL or scH position. Thus the associated peptide material is dissociated from the DNA by the applied current and does not affect the electrophoretic mobility of the plasmid.

Methylation and Restriction Analysis

Enzymes were purchased from New England BioLabs. 8–10 units of dam methyltransferase and 3.2 mM S-adenosylmethionine were used for the methylation of 200–300 ng scH RepFIC DNA. Conditions as suggested in the methylation kit were adequate for methylating scL DNA. Otherwise buffers supplied by the manufacturer were used as directed. Approximately 3 or 4 units of restriction enzyme were used per lane, and reactions were allowed to proceed for 30–45 minutes unless otherwise stated. When DpnI restriction was carried out as a time course, the times were 15, 30 and 45 minutes. Molecular weight (MW) standard were purchased from Roche Diagnostics (III and V). Agarose gel electrophoresis was carried out in 0.8% agarose, except for the separation of small fragments (MW standard V), carried out in 4% agarose.

Piperidine Hydrolysis

Piperidine was used at the same concentration as in Maxam-Gilbert sequencing, but the temperature was lowered from 90° to 86°. Times were as indicated.

Dissociating the Nucleoprotein Complex

The DNA was prepared as above, except that after lysis and centrifugation the suspension was made 0.3M sodium acetate and maintained at 50° for 30 minutes. The suspension was chilled on ice, guanidinium hydrochloride was added as specified in the kit, and the procedure recommended by the manufacturer was followed.

DNA Sequencing

All samples used for sequencing had to be treated for dissociation of the nucleoprotein complex (salt stripping).

AmpliCycle Sequencing Kits (Perkin Elmer) were used with [α-$^{33}$P]-dATP (Dupont). In order to demonstrate that the scL phenotype, although heritable, did not involve mutations, 5 variants were sequenced with the parent plasmid in their entirety (3 kb). The six reactions were loaded side by side for each of the four deoxynucleotides.

Transformation

Bacteria were transformed by electroporation with and E. coli Pulser (Bio-Rad) as recommended by the manufacturer, with 50–100 ng DNA. Incubation before plating was carried out for 90 minutes at 37° in SOC medium (Bio-Rad). Addition of methylation supplements is specified for each experiment.

Nucleotide Sequence Accession Number

The RepFIC sequence has been assigned GenBank accession number M16167.

Plasmid of Altered Mobility in Agarose Gel Electrophoresis

After transforming hosts such as C6060 for ion mutants with the miniplasmid RepFIC under specific growth conditions, it was found that the DNA was maintained in an altered structural form. When agarose gel electrophoresis was conducted in the absence of intercalating agents, the DNA had a lower electrophoretic mobility than what is usually called supercoiled (sc) plasmid. The mobility is similar but presumably not identical to that of nicked-relaxed plasmid or plasmid dimers. The reduced electrophoretic mobility indicates a reduced helical density or lower linking number (Kornberg and Baker, 1992). Plasmid in the altered structure does not penetrate 0.8% gels unless it is first treated with salt.

It has been shown by the above that the miniplasmid RepFIC is maintained in E. coli hosts in two main conformations of different linking number. One is of low helical density and the other of higher helical density. Both are supercoiled, although only the latter has been referred to as sc in the literature. Because these two forms exist in different proportions depending on the growth state of the culture, it is assumed that these two forms represent different phases of the replicative cycle.

The plasmid in the scL form has been shown to be fully methylated at frequent loci that are not canonical. Given the nature of the plasmid and the frequency of methylation, it is assumed that at least some of these sites are in the origin region. These same loci are not detected by the enzyme DpnI, which is specific for full methylation, in the scH form of the plasmic. Assuming that scH and scL are both intermediates in the same replicative cycle, these loci are presumably not hemimethylated. The methylation status identifies scL plasmid as not having undergone duplication, and scH plasma as being post-replicative. This situation is somewhat different from the E. coli chromosomal origin, where there are 11 canonical GATC sites. The OriC loci are also hemimethylated after duplication, but there is only a 13 minute delay before remethylation (Campbell and Kleckner, 1990), the latter nor depending on the DNA conformation. The methylation reaction of RepFIC-type origins will also be referred to as conformationally-dependent-deoxynucleotide-methyl transfer (Cdnm).

Resolution of Z-DNA structures has shown that the imidazole ring of guanines, which lies in the major groove of B-DNA structures, forms part of the outer wall of the Z-DNA molecules (Wang et al., 1979). Under these conditions the N7 of guanine protrudes and is accessible to chemical modification. It has been demonstrated that such guanines are over susceptible to in vitro methylation by the reagent dimethylsulfate (DMS), Johnston and Rich, 1985. One possibility is that scL DNA is like Z-DNA, and that enzymatic catalysis of scL methylation mirrors the chemical methylation reaction of DMS.

The Cdnm fully methylated loci of scL DNA were detected by digestion with the enzyme DpnI, which is specific for fully methylated adjacent purines on two DNA strands. Their close spacing resulted in the DpnI shredding the DNA. Thus, although critical for demonstrating Cdnm full methylation, the shredding assay is qualitative rather than quantitative. Mapping of Cdnm loci requires different methodology that maintains the sugar-phosphate backbone intact.

The scL post-replicative obligate product that is hemimethylated at all loci has not been isolated. This, as well as scL maintenance of the plasmid in lon hosts, may indicate that the hemimethylated product is cleared of all proteins by Lon-protease, a cellular enzyme, and is then returned to scH-helical density. As only canonical sites are fully methylated in scH plasmid, it is known that the duplicated plasmid is methylated after the scL→scH transition.

Possible explanations for not detecting the hemimethylated scL products are as follows: Both the clearing process and the following increase in helical density are rapid steps. In the absence of clearing, full methylation of scL DNA is also rapid. Hemimethylated scL DNA that is not otherwise processed is targeted for degradation. The last possibility would prevent the inheritance of plasmids were replication was aborted by cell division, and could explain sequestering effects that have been observed for hemimethylated replication origins (Lu et al., 1994; Russell and Zinder, 1987).

Some of the physical and chemical properties of the scL precursor were characterized because of the serendipitous finding that, after highly enhanced transformation by the addition of cysteine and specific growth conditions, the scL phenotypes was imprinted. Based on the fact that RepA is a cysteine containing protein that can lower helical density, and that is synthesis is translationally coupled to a cysteine containing peptide, it appears that the most likely cause of imprinting was the stimulated synthesis of the protein imitator of replication RepA. It appears that when plasmid in the altered structure is used in transformations stimulated synthesis is retained, because the structure remains imprinted. Plasmid in the altered structure appears to be associated with dam-methyltransferase that is co-transferred in transformations, because when it is removed by salt stripping, transferred plasmids reboot. This suggests that both removal and replacement of the methyltransferase occur in vivo at specific times during the replicative cascade. "Inheritance" of the methyltransferase could explain methylation imprinting in other organisms.

The increase of transformation efficiency was unexpectedly large. RepFIC, like its close relatives R1 and R100, codes for four cysteine-containing polypeptides (Masai et al., 1983; Saadi et al., 1987). It has been shown that the RepA gene does not have an effective ribosomal binding site for translation of its transcript. Thus, the translation of RepA is coupled to that of RepC or of uORF, but mostly to the latter (Blomberg et al., 1992; Wagner et al., 1987; Wu et al., 1992). UORF contains two cysteines out of 24 amino acids and is made at levels ten times higher than RepA. Thus, the biosynthesis of repA is dependent on an adequate supply of cysteine. It appears that the deregulated synthesis of uORF-RepA ultimately imprints the somewhat deleterious maintenance of the plasmid, since cysteine-recovered transformants grow as snakes, unless filamentous growth is relieved by the addition of certain ions to the growth medium.

The coupled translation of uORF-RepA, despite broad differences in the RepA sequence of the different E. coli replicons, involves a shift at 23.cys or uORF to 1.met of RepA. The coding sequence at the frameshift, absolutely conserved, is TGTG. The first three nucleotides code for cysteine and the second, third and fourth nucleotides provide the less common methionine starting codon (GTG) by a −2 shift. Thus the frameshift, presumably occurring after incorporation of cysteine at position 23 of uORF, provides an effective mechanism for limiting the levels of uORF-RepA.

FIG. 6 shows a scheme that describes plasmid replication integrated into the cell cycle. The conformation of the plasmid, in the normal B-helix and fully methylated at GATC sites, is changed to a form of lower helical density, as illustrated in step I of FIG. 6. The plasmid DNA of lower helical density becomes fully methylated at Cdnm loci (step II). Duplication proceeds, (step III), and the totally hemimethylated product is cleared of associated proteins, including the dam-methyltransferase (step IV, or "Lon-reboot"). The product of step IV, conformed to B-helical density, is fully methylated at canonical loci (step V). When the methyltransferase is not removed in the reboot step, the putative hemimethylated product of step III can be fully methylated at both canonical and non-canonical loci, and replication resumes.

Rebooting can occur not only by the function of Lon, but also during transformation (Table 2, row 5). In this case, the supply of cysteine is adequate. One interpretation of the result is that after electroporation and DNA entry, fresh medium is added, and the cells are allowed go grow for 90 minutes before selective plating. During this time two cell divisions take place, which has been checked by plating without selection. When the plasmid enters free of proteins, it probably does not interfere with cell division. As the plasmid is already at low helical density, RepA is not required and DNA synthesis initiates. The presence of homocysteine in the medium maintains the MetR regulon, which probably includes the dam-methyltransferase, active. Therefore, the methyltransferase is loaded appropriately at every opportunity. Full appropriate methylation stabilized the scL conformation, and results in a lower requirement for RepA and thus for cysteine. This interpretation suggests that RepA plays no direct part in DNA synthesis, as we already known from in vitro cell-fress systems (Kornberg and Baker, 1992).

The significance of the scL conformation remains in question. The conformational shift appears to occur prior to processive DNA synthesis. It has been shown in vivo that the primed start site of replication is located at ssr (Maas and Wang, 1997). Masai and Arai (Masai and Arai, 1989) have shown that in vitro, when a different and exogenously supplied priming system is used, the start site is located 400 bp downstream. This could indicate that in vivo, priming, conformational shift, and non-processive initiatory DNA synthesis are regulated steps that give way to processive replication. This could place the requirement for RepA after priming and before the first non-processive DNA synthesis.

It appears that in the scL conformation, the origin favors a 4-stranded DNA structure which permits primary and non-processive DNA synthesis. Such stacked 4-stranded structures have been demonstrated in cytosine-rich DNA (Berger et al., 1996). And the RepFIC origin is in fact cytosine rich. It appears that scL DNA can accommodate newly synthesized strands in the origin-terminus region. Under such conditions, duplicated DNA would remain associated as plasmid doublets until a conformational change permits them to segregate.

The process of the present invention can be applied to relaxed transforming DNA, as is commonly used in cloning experiments, as well as to supercoiled DNA. As there are many plasmid that replicate by the same mechanism as RepFIC, any one of them can be used in this way to make libraries. The process of the present invention can be used with any desired vector or host.

The foregoing description of the specific embodiments will so fully reveal the general nature of the invention that others can, by applying current knowledge, readily modify and/or adapt for various applications such specific embodiments without undue experimentation and without departing from the generic concept, and, therefore, such adaptations and modifications should and are intended to be comprehended within the meaning and range of equivalents of the disclosed embodiments. It is to be understood that the phraseology or terminology employed herein is for the purpose of description and not of limitation. The means, materials, and steps for carrying out various disclosed functions may take a variety of alternative forms without departing from the invention.

Thus, the expressions "imeans to . . . " and "means for . . . ", or any method step language, as may be found in the specification above and/or in the claims below, followed by a functional statement, are intended to define and cover whatever structural, physical, chemical, or electrical element or structure, or whatever method step, which may now or in the future exist which carries out the recited functions, whether or not precisely equivalent to the embodiment or embodiments disclosed in the specification above, i.e., other means or steps for carrying out the same function can be used; and it is intended that such expressions be given their broadest interpretation.

What is claimed is:

1. In a method for transferring DNA into host cells comprising subjecting said host cells to electroporation in the presence of said DNA, the improvement comprising conducting said electroporation, adding homocysteine to the cells immediately following electroporation and during selection, and adding a source of cysteine during selection.

2. The method according to claim 1 wherein the cysteine during selection is present in an amount of 400 micrograms/ml.

3. The method according to claim 1 wherein the source of cysteine is selected from the group consisting of cysteine and glutathione.

4. The method according to claim 1 wherein the medium further contains ferrous sulfate and magnesium ion.

5. The method according to claim 1 wherein the host is *E. coli*.

6. The method according to claim 4 wherein the magnesium ion is present as magnesium sulfate.

7. The method according to claim 5 wherein the DNA is transferred using a replicon selected from the group consisting of plasmids which replicate in *E. coli*.

8. A kit for replication comprising a polylinker with a plurality of restriction sites, a source of cysteine for selection, and a combination of homocysteine, ferrous sulfate, and magnesium ion.

9. The kit according to claim 8 wherein the magnesium ion is present as magnesium sulfate.

10. The kit according to claim 8 further comprising a plasmid replicon selected from the group consisting of plasmids which replicate in *E. coli*.

* * * * *